US008535665B2

(12) United States Patent
Wang

(10) Patent No.: US 8,535,665 B2
(45) Date of Patent: Sep. 17, 2013

(54) PROCESS FOR IDENTIFICATION OF MOLECULAR MIMICRY AND THE USES THEREOF

(76) Inventor: Huiru Wang, Willowbrook, IL (US)

(*) Notice: Subject to any disclaimer, the term of this patent is extended or adjusted under 35 U.S.C. 154(b) by 201 days.

(21) Appl. No.: 12/310,174

(22) PCT Filed: Aug. 17, 2007

(86) PCT No.: PCT/US2007/018258
§ 371 (c)(1),
(2), (4) Date: Feb. 13, 2009

(87) PCT Pub. No.: WO2008/021493
PCT Pub. Date: Feb. 21, 2008

(65) Prior Publication Data
US 2009/0324582 A1 Dec. 31, 2009

Related U.S. Application Data

(60) Provisional application No. 60/822,916, filed on Aug. 18, 2006.

(51) Int. Cl.
*A61K 39/395* (2006.01)
*G01N 33/53* (2006.01)
*C12Q 1/70* (2006.01)

(52) U.S. Cl.
USPC ............ 424/130.1; 435/5; 435/7.2; 435/7.31; 435/7.22; 424/184.1; 424/202.1

(58) Field of Classification Search
None
See application file for complete search history.

(56) References Cited

U.S. PATENT DOCUMENTS

| | | | |
|---|---|---|---|
| 5,637,677 A * | 6/1997 | Greene et al. ............ | 530/333 |
| 5,712,245 A | 1/1998 | Blaas et al. | |
| 5,929,220 A | 7/1999 | Tong et al. | |
| 6,992,234 B2 | 1/2006 | Roopenian | |
| 2005/0169929 A1 | 8/2005 | Himmler et al. | |
| 2005/0186223 A1 | 8/2005 | Williams et al. | |

FOREIGN PATENT DOCUMENTS

WO    WO 9509182    4/1995

OTHER PUBLICATIONS

Wallberg et al. (Eur. J. Immunol. 2003. 33:1539-1547).*
Bogdanos et al (Clinical & Development Immunology 2005 vol. 12, p. 217-224).*
Mejias et al. (Antimicrobial Agents and Chemotherapy, 2004, vol. 48, p. 1811-1822).*
Mejias et al. (The Pediatric Infectious Disease Journal, 2005, vol. 24, p. 189-197).*
Hirabayashi et al. (Journal of Virological Methods, 1996, vol. 61, p. 23-36).*
Bogdanos et al. (Clinical & Developmental Immunology, 2005, vol. 12, p. 217-224 of record on Jan. 3, 2011).*
Okuno et al. (Journal of Virology, 1994, vol. 68, p. 517-520).*
Simmons, C. et al., Prophylactic and Therapeutic Efficacy of Human Monoclonal Antibodies against H5N1 Influenza PloS. Med. (2007), 4(5): e178.
Hanson, B. et al., Passive immunoprophylaxis and therapy with humanized monoclonal antibody specific for influenza A H5 hemagglutinin in mice, Respiratory Research (2006), 7:126.
Roskoski, Robert, The ErbB/HER receptor protein-tyrosine kinases and cancer. (2004), Biochem.Biophys. Res. Commun. 319: 1-11.
Oleszak, E. et al., Inducible Nitric Oxide Synthase in Theiler's Murine Encephalomyelitis Virus Infection, Clin. Microbiol. Rev. (2004), 17: 174-207.
Robbe, Catherine et al., Structural diversity and specific distribution of O-glycans in normal human mucins along the intestinal tract, Biochem. J. (2004) 384, 307-316.
Mackay, I. and F. Rosen, Autoimmune diseases. New. Engl. J. Med. (2001), 345, 340-350.
Yamada, M. et al., Common Immunologic Determinant between Human Immunodeficiency Virus Type 1 gp41 and Astrocytes, J. Virol. (1991), 65: 1370-1376.
Beisel K. W. et al. "A neutralizing monoclonal antibody against Coxsackievirus B4 cross-reacts with contractile muscle proteins" Microbial Pathogenesis, Academic Press Limited, New York, NY, US, vol. 8, No. 2, Feb. 1, 1990, pp. 151-156, XP023312919 ISSN: 0882-4010 [retrieved on Feb. 1, 1990].
Oldstone, Michael, "Virus-induced autoimmunity: Molecular mimicry as a route to autoimmune disease" Journal of Autoimmunity, London, GB, vol. 2, Jun. 1, 1989, pp. 187-194, XP022993289 ISSN: 0896-8411 [retrieved on Jun. 1, 1989].
Srinivasappa J, et al: Molecular Mimicry Frequency of Reactivity of Monoclonal Antiviral Antibodies with Normal Tissues, Journal of Virology, vol. 57, No. 1, 1985, pp. 397-401, XP002563736 ISSN: 0022-538X.

* cited by examiner

*Primary Examiner* — Agnieszka Boesen
(74) *Attorney, Agent, or Firm* — McDonnell Boehnen Hulbert & Berghoff LLP

(57) ABSTRACT

The present invention discloses a process for simple and rapid detection and identification of molecular mimicry or mimic antigens or molecules existing in/on humans, animals and plants. The molecular mimicry can be related to infections, autoimmune diseases, cancers, obesity and other disorders. Therefore, novel methods for the diagnosis, prevention, and treatment of infections, autoimmune diseases, cancers, obesity and other disorders obtainable based on these mimic antigens or molecules can be developed. Furthermore, the present invention also reveals a new functional mechanism of vaccine and passive immunity and novel vaccines obtainable based on the new mechanism.

3 Claims, 13 Drawing Sheets

Human - Fetal
Small Intestine

Anti-RSV

Anti-RV

Anti-HBV

Anti-HAV

Mouse Adult

| | Kidney | Spleen |
|---|---|---|
| Anti-Adeno |  |  |
| Anti-EBV |  |  |

MDCK + H5N1

PROCESS FOR IDENTIFICATION OF MOLECULAR MIMICRY AND THE USES THEREOF

CLAIM OF PRIORITY

This application claims priority to U.S. Provisional Patent Application Ser. No. 60/822,916, filed Aug. 18, 2006, entitled "Process for the Identification of Mimic or Identical Antigens of Pathogenic Organisms and the Uses Thereof," the entire specification and disclosure of which is herein incorporated by reference.

FIELD OF INVENTION

The present disclosure relates generally to the fields of biology, medicine and epidemiology, and in particular, to one or more processes for diagnosing, preventing and/or treating infections, autoimmune diseases, cancers and/or other diseases. More specifically, the present disclosure relates to a process for the identification of antigens that mimic with antigens of pathogenic organisms or infectious agents, and the uses thereof.

BACKGROUND OF THE INVENTION

Molecular mimicry is defined as the theoretical possibility that sequence or structure similarities between foreign and self-peptides are sufficient enough to result in the cross-activation of autoreactive T or B cells by pathogen-derived peptides. The prerequisite for molecular mimicry to occur is thus the sharing of the immunodominant epitope between the pathogen and the immunodominant self sequence that is generated by a cell or tissue. The mechanism by which pathogens have evolved, or obtained by chance, similar amino acid sequences or the homologous three-dimensional crystal structure of immunodominant epitopes remains a mystery (Wikipedia, the free encyclopedia).

An autoimmune disease occurs when a host fail to recognize self antigens as "self". Growth in the study of autoimmunity has resulted in more and more people being diagnosed with an autoimmune disease which affects approximately 1 in 31 people within the general population. However, rapid diagnosis and effective prevention and treatment of autoimmune diseases have been very limited due to the unknown causes and pathogenesis mechanisms of these diseases. In recent years, there has been tremendous growth in the study of the several different ways in which autoimmunity can occur; one of which is molecular mimicry.

An infectious disease is a clinically evident disease of humans or animals. Information collected by the World Health Organization on global deaths shows that worldwide mortality due to infectious diseases is as high as 25.9% of all deaths, or 14.7 million deaths in 2002. The top three infectious disease killers which caused 58% of deaths caused by infectious disease were mainly virus related infections such as lower respiratory infections, HIV/AIDS and diarrheal diseases. The most effective medical approaches to viral infections so far are vaccinations. Other significantly effective medicines for viral infections are limited. Virus entry into the host cells by binding receptor or co-receptor (host cell surface factors that bind to native virions). The receptors and co-receptors are major determinants of viral tropism, limiting the host range, and probably the nature of the age-dependent (affect only infant or young children). The tissue distribution of receptors and co-receptors in part determines the symptoms of infections. Therefore, precise knowledge of the viral receptors and co-receptors will help to develop new antiviral and vaccine strategies. Such studies have been largely left uninvestigated due to the lack of a simple and efficient technique to identify and purify receptors and co-receptors of infectious agents. Molecular mimicry can be a useful tool for this application.

Cancer is a disease characterized by a population of cells that grow and divide without respect to normal limits, invade and destroy adjacent tissues, and may spread to distant anatomic sites through a process called metastasis. Cancer causes about 13% of all deaths. Experimental and epidemiological data imply a causative role for viruses and they appear to be the second most important risk factor for cancer development in humans, exceeded only by tobacco usage. The role of molecular mimicry in the pathogenesis of infection-related cancers has never been explored.

To determine which epitopes are shared between pathogen and self, large protein databases are used. The largest protein database in the world, known as the SWISS-PROT database, has shown reports of molecular mimicry becoming more common with expansion of the database. Due to the amino acid variation between different proteins, molecular mimicry should not happen from a probability standpoint. The possibility exists, then, for variability within amino acid sequence, but similarity in three-dimensional structure between two peptides can be recognized by T or B cell clones. This, therefore, uncovers a flaw of such large databases. They may be able to give a hint to relationships between epitopes, but the important three-dimensional structure cannot yet be searched for in such a database.

SUMMARY OF THE INVENTION

The present disclosure relates to a simple and efficient process for the rapid identification of molecular mimicry or mimic antigens or molecules being expressed in humans, animals or plants that mimic with antigens of pathogenic organisms or infectious agents specific to infections. The process according to the present disclosure is essentially characterized by the following operations:

1) the identification of at least one antibody that reacts with a pathogenic organism;

2) the binding of the identified antibody or antibodies to cells or tissues or organs or extract of cells or tissues or organs of humans, animals or plants either in vivo or in vitro;

3) the detection of the presence and location of the antibody or antibodies binding to cells or tissues or organs or extract of cells or tissues of humans, animals or plants, in a variety of ways well known to those of ordinary skill in the art;

4) the detection of the function of the antigens binding to the antibody or antibodies, in available animal experiments and/or cell or tissue culture systems, using the antibody or antibodies in a variety of ways well known to those of ordinary skill in the art;

5) the purification of the antigens binding to the antibodies, using the antibody or antibodies in a variety of ways well known to those of ordinary skill in the art;

6) the identification of the antigens bound to the antibodies, in a variety of ways well known to those of ordinary skill in the art; and 7) the application of the antibodies, the antigens identified, derivatives, analogs, agonists, antagonists, variants, mutants, fragments, synthetic peptides, recombinant antigens or any other forms of the antigens for the diagnosis, prevention and treatment of infections, autoimmune diseases, cancers, obesity and other disorders related to the antibodies and/or the antigens.

A key feature of the present disclosure is a novel, simple and efficient strategy for the detection, purification and identification of pathogenically mimicry or mimic antigens or molecules in healthy humans, animals or plants. These mimic antigens or molecules can be receptors, coreceptors, ligands of recognizing factors of infectious agents, or key factors of pathogenesis of infections, autoimmune diseases, cancers, obesity and other disorders.

The present disclosure also relates to the development of novel methods of application of the identified pathogenically mimic antigens or molecules, including methods for the prevention, diagnosis, and treatment of infections, autoimmune diseases, cancers, obesity and other disorders obtainable based on these antigens. Such methods of application include but not limited to the uses of the selected antigens thereof and/or their derivatives and/or their antibodies for the formulation of diagnostic kits for the specific pathogenic agent, or in general for the infections and/or diseases, including autoimmune diseases, cancers, obesity and other disorders with known or unknown etiology and/or pathogenesis; the uses of the selected antigens thereof and/or their derivatives and/or their antibodies for the prevention and therapy of the diseases induced by said antigens or antibodies; and the uses of the selected antigens thereof and/or their derivatives and/or their antibodies to the fields of epidemiology and developmental and evolutionary biology.

Accordingly, a principal object of the present disclosure is to provide a simple and efficient process for the rapid identification of antigens that mimic with antigens of pathogenic organisms or infectious agents, and the uses thereof. Numerous other objects, features and advantages of the present disclosure will become readily apparent from the detailed description and from the claims which follow.

BRIEF DESCRIPTION OF THE DRAWINGS

FIG. 10 is a graphical representation of prevention of binding of inactivated influenza A virus strain H5N1 to MDCK cells by anti-virus antibodies and human sera.

DETAILED DESCRIPTION OF THE PREFERRED EMBODIMENT(S)

Figure 1:
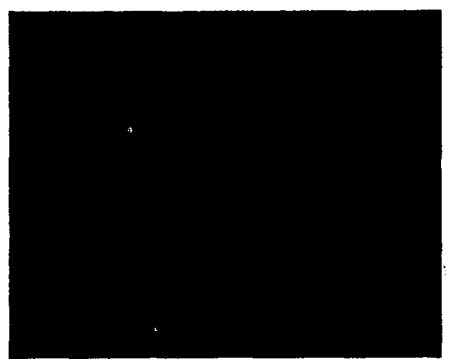
FIG. 1 is a graphical representation of binding of anti-viral sera to tissue section of small intestine of human fetal.
Figure 1:
Figure 1:
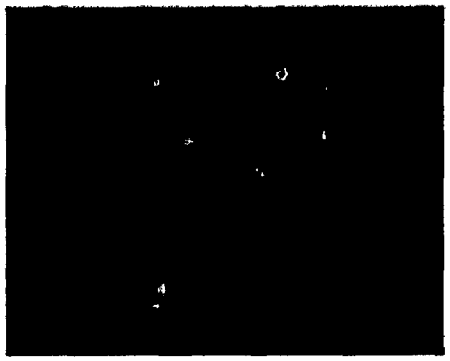
Figure 1:
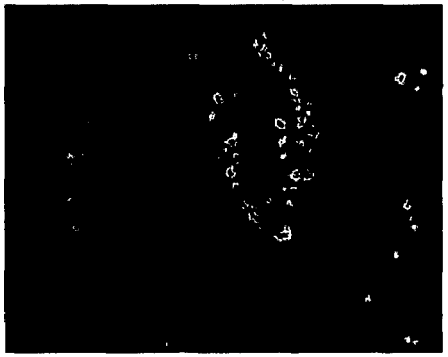

While the present disclosure is susceptible of embodiment in many different forms, there will be described herein in detail, preferred and alternate embodiments of the present disclosure. It should be understood however, that the present disclosure is to be considered an exemplification of the principles of the invention and is not intended to limit the spirit and scope of the invention and/or claims of the embodiments illustrated.

Aspects of the present invention are based on a process or method for simple and rapid detection and identification of molecular mimicry or mimic antigens or molecules existing in/on humans, animals and plants. The molecular mimicry can be relevant to infections, autoimmune diseases, cancers, obesity and other disorders. Therefore, novel methods for the diagnosis, prevention, and treatment of infections, autoimmune diseases, cancers, obesity and other disorders obtainable based on these mimic antigens or molecules can be developed. Furthermore, the present invention also reveals a new functional mechanism of vaccine and passive immunity as well as new vaccines obtainable based on the new mechanism.

Pathogens and Antibodies

One aspect of the present invention relates to organisms responsible for illness and/or organisms related to life evolution and antibodies to these organisms. As used herein, the term "infections" refers to the detrimental colonization of a host organism by a foreign species, a "pathogen" or "infectious agent" refers to a microscopic organism though the definition is broader. Pathogens or infectious agents specific to infections suitable for use in this process include, but are not limited to, viruses, bacteria, parasites, fungi, viroids, prions, etc., without limitation.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, F.sub.ab, F.sub.ab' and F(ab').sub.2 fragments, and an Fab expression library. In general, an antibody molecule obtained from humans relates to any of the classes IgG, IgM, IgA, IgE and IgD, which differ from one another by the nature of the heavy chain present in the molecule. Certain classes have subclasses as well, such as IgG.sub.1, IgG.sub.2, and others. Furthermore, in humans, the light chain may be a kappa chain or a lambda chain. Reference herein to antibodies includes a reference to all such classes, subclasses, antibody fragments and types of human antibody species. Natural occurring antibodies are found in blood or other bodily fluids of vertebrates. Antibodies suitable for use in this process can be specific for any organism or infectious agents of interest which is related to an infection, an auto-immune disease or a tumor in human, animals or plants.

Preferably antibodies to viruses suitable for use in this process include but not limited to any types of antibodies or antibody fragments to dsDNA viruses including but not limited to adenoviridea, herpesviridea, papovaviridea, poxyviridea; the ssDNA viruses including but not limited to circoviridea, geniniviridae, parvovirinae; dsRNA viruses including but not limited to bimaviridae, reoviridea, (+)sense RNA viruses including but not limited to astroviridea, caliciviridea, coronaviridea, flaviviridea, picornaviridea, potyviridea, tabamoviridea, togaviridea; (−)sense RNA viruses including but not limited to filoviridea, pararnyxoviridea, pneumovirinae, rhabdoviridea, arenavirus, bunyaviridea, orthomyxoviridea; RNA reverse transcribing viruses including but not limited to retroviridea; DNA reverse transcribing viruses including but not limited to badnavirus, caulimoviridea, hepadnaviridea; satellites including but not limited to tobacco necrosis virus satellite; hepatitis delta virus; viroids including but not limited to potato spindle tuber viroid, and agents of spongiform encephalopathies. More specifically, antibodies to viruses include but not limited to any types of antibodies to reovirus, rotavirus, cytomegalovirus, influenza virus including avian influenza A virus, Epstein-Barr virus, hepatitis virus, HIV, HTLV, papilloma virus, polio virus, parainfluenza virus, measles virus, mumps virus, respiratory syncytial virus, shipping fever virus, Western and Eastern encephalomyelitis virus, Japanese B encephalomyelitis virus, Russian spring-summer encephalomyelitis virus, hog cholera virus, pox virus, rabies, virus, distemper virus, foot and mouth disease virus, rhinovirus, Newcastle disease virus, vaccinia virus; and pseudorabies virus, etc without limitation.

Antibody Binding

One aspect of the present invention relates to binding of an antibody against a pathogenic microorganism to any types of cells or tissues or organs or extract of cells or tissues or organs of a human, an animal or a plant in vitro and/or in vivo. The antibody can be either purified or conjugated with a moiety such as biotin, fluorescents or any other detectable means known in the art. A secondary or third reagent can be used if necessary for the detection of the antibody/antigen binding. Binding of an antibody to cells or tissues or organs in vivo suitable for use in this process includes but not limited to administration of an antibody to a human, an animal or a plant. A selective antibody can be administered intravenously, intraperitoneally, intramuscularly, subcutaneously, intracavity, transdermally, inhalantly or with other approaches. The binding antibodies usable in this invention can be also used for in vivo imaging, wherein for example a selective antibody labeled with a detectable moiety is administered to a human or an animal, preferably into the bloodstream, and the presence and location of the labeled antibody in the host is detected. The antibody can be labeled with any moiety that is detectable in human, animals, or plants whether by nuclear magnetic resonance, radiology, fluorescence, or other detection means known in the art.

Combination of in vivo and in vitro methods of antibody binding and detection as mentioned above can be also used preferably in animals. For example, a selected antibody labeled with a moiety can be administered to an animal, the antibody will bind to its mimic antigen in vivo, followed by scarification of the animal, collection of tissue or organ samples and detection of the bound antibody in vitro using detection means known in the art.

The methods for detection of an antibody-antigen binding suitable for use in this process include but not limited to flow cytometry, immunofluorocent staining, immunochemistry staining, Western blot, ELISA or any other ordinary skill for the detection of antigen/antibody binding known in the art.

Examples of molecular mimicry between various viral pathogens and mouse and human tissues or organs, detected by binding of anti-viral antibodies to tissue sections of human fatal, newborn pups and adult mouse and a cell line, are shown in FIG. 1-7.

Cells, Tissues, Organs and Molecular Mimicry

Types of cells or tissues or organs of humans, or animals or plants, to which a antibody to bind according to the present invention can be any types of cells being cultured in vitro including but not limited to various cell lines and primary cells known in the art; any types of cells being obtained from fresh tissues; any types of tissue sections or smears of fresh, frozen or fixed tissues or organs; homogenates of tissues or organs, any types of organ parts, or any types of extracts of cells, tissues or organs; etc., without limitation.

As used herein, the term "antigen" or "immunogen" refers to a molecule that stimulates an immune response. The modern definition encompasses all substances that can be recognized by the adaptive immune system. Antigens are usually proteins or polysaccharides. This includes parts (coats, capsules, cell walls, flagella, fimbrae, and toxins) of bacteria, viruses, and other microorganisms.

The term "molecular mimicry" or "mimic antigen/molecule" or "antigen/molecule mimics" as used herein refers to the theoretical possibility that sequence or structure similarities between foreign and self-peptides are sufficient enough to result in the cross-activation of autoreactive T or B cells by pathogen-derived peptides. A single antibody or TCR (T cell receptor) can be activated by even a few crucial residues which stresses the importance of structural homology in the theory of molecular mimicry. The prerequisite for molecular mimicry to occur is thus the sharing of the immunodominant epitope between the pathogen and the immunodominant self sequence or structure that is generated by a cell or tissue. In some cases, pathogenic mimics can possess a structural architecture that differs markedly from that of the functional homologues. It has been hypothesized that these virulent proteins display their mimicry through molecular surfaces that mimic host protein surfaces (protein fold or three-dimensional conformation), which have been obtained by convergent evolution.

An antigenic or molecular mimicry according to the present invention can exist on the surface, across cell membrane, inside or outside of cells of tissues or organs of humans, animals or plants during their either part or intact period of life time from embryo, fetal, newborn, young child to adult. The tissues or organs of humans and animals can be but not limited to epithelium and glands; connective tissue; muscle including smooth, skeletal and cardiac muscle; nervous tissue including central nervous system (CNS) and peripheral nervous system (PNS); cartilage, bone and joints; extracellular matrix; blood and hemopoiesis; bone marrow; cardiovascular system including heart, arteries, capillaries and veins; respiratory system including lungs, bronchial tree, alveolar duct and alveoli, digestive system including oral cavity, esophagus, stomach, small intestine (duodenum, jejunum, and ileum), and large intestine (cecum, colon, rectum, anal canal and appendix), salivary glands, pancreas, liver, bile duct and gallbladder; urinary system including kidneys, ureter, bladder, and urethra; female reproductive system including ovaries, oviducts, uterus and vagina; male reproductive system including testes, genital ducts, penis, seminal vesicles, prostate gland, and bulbourethral glands; lymphois (immune) system including lymph nodes, thymus and spleen; endocrine glands including pineal body, pituitary gland, thyroid gland, parathyroid glands and suprarenal glands; integument including skin and its appendages, sweat glands, sebaceous glands, hair and nails.

Animal Experiments

Figure 12:
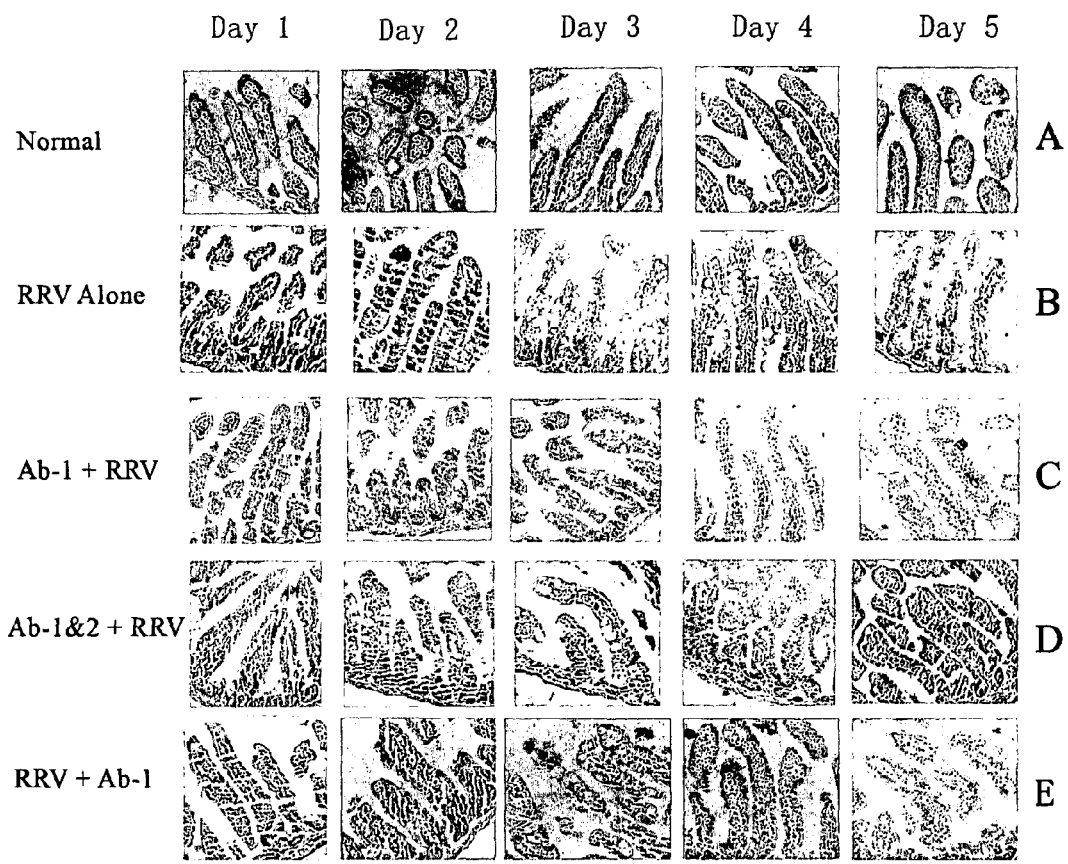
FIG. 12 is a graphical representation of histological changes of small intestine of mouse pups treated with antibodies to rotavirus before and after rotavirus infection.
Figure 13:
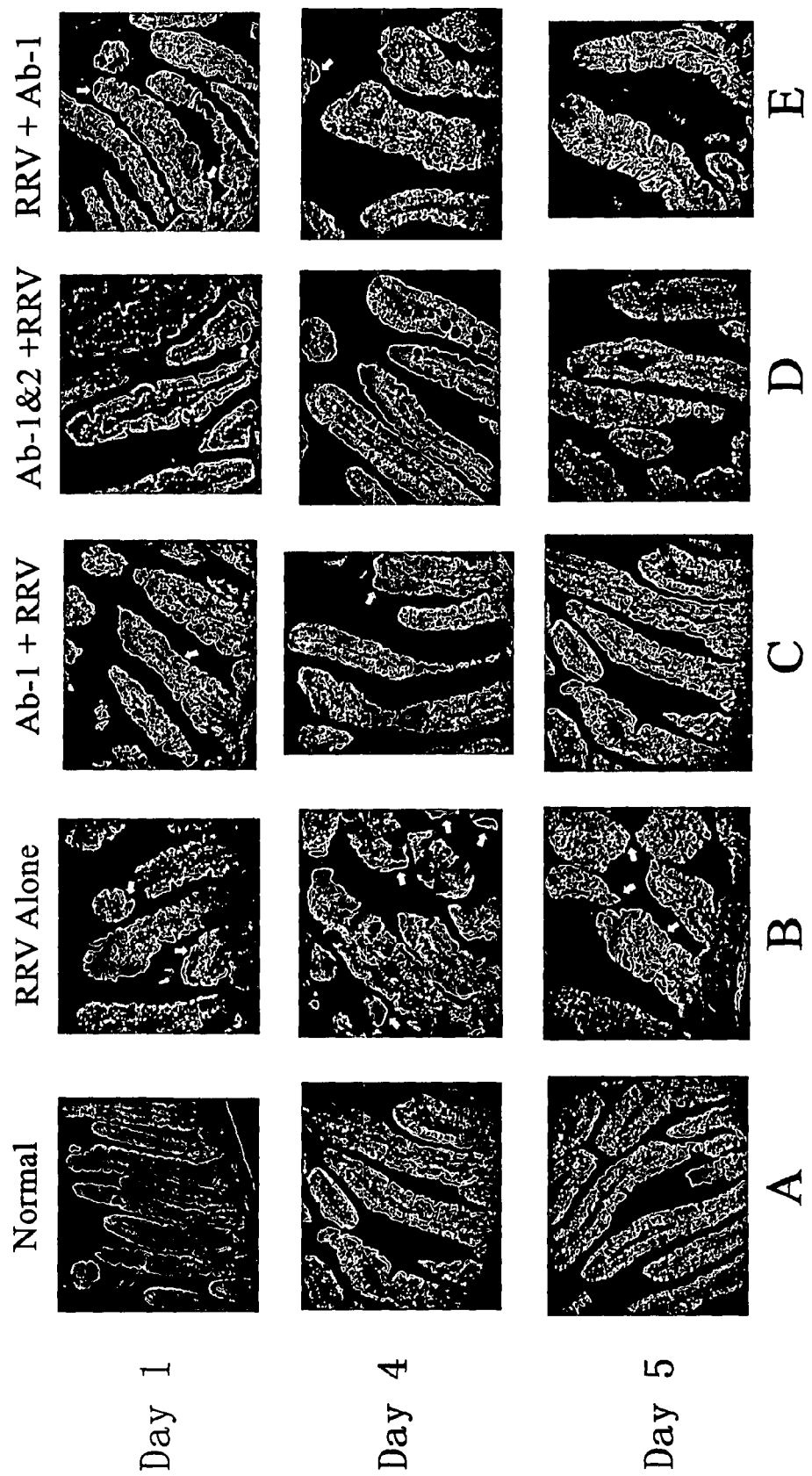
FIG. 13 is a graphical representation of immunofluorescent stain for rotavirus antigen VP6 on tissue section of small intestine of mouse pups treated with anti-rotavirus antibodies before and after rotavirus infection.

Another subject of the present invention is the use of the selected antibodies according to the present invention in animal experiments for the detection of the function of the mimic antigens or molecules binding to the antibodies in a variety of ways well known to those of ordinary skill in the art. A selected antibody to a infectious pathogen (a virus strain for example) can be administered to an animal (a mouse for example) for a period of time sufficient for the antibody to bind to the mimic antigens or molecules existing in the host of the infectious pathogen in vivo before the infection of the pathogen. In the case that the mimic molecule is the receptor or factors related to the entry of the pathogen, the antibody can block the mimic antigen or molecule and prevent the entry of the pathogen into the target cells of the animal. Thereof the animal will not be or lightly affected by the pathogen. The same animal model can also be used to determine the therapeutic effect of the selected antibodies on the related infections by administering a selected antibody against a pathogen to an animal after the infection. The process will be useful to evaluate the function of a molecular mimicry and to screen candidate antibodies and other reagents for prevention and treatment of infections in vivo. An example of prevention and treatment of rotavirus infection with anti-rotavirus antibody in a mouse model is as described as in the part of Exemplification of the application (FIG. 12-13).

Cellular or Tissue Culture Assay

Figure 8:
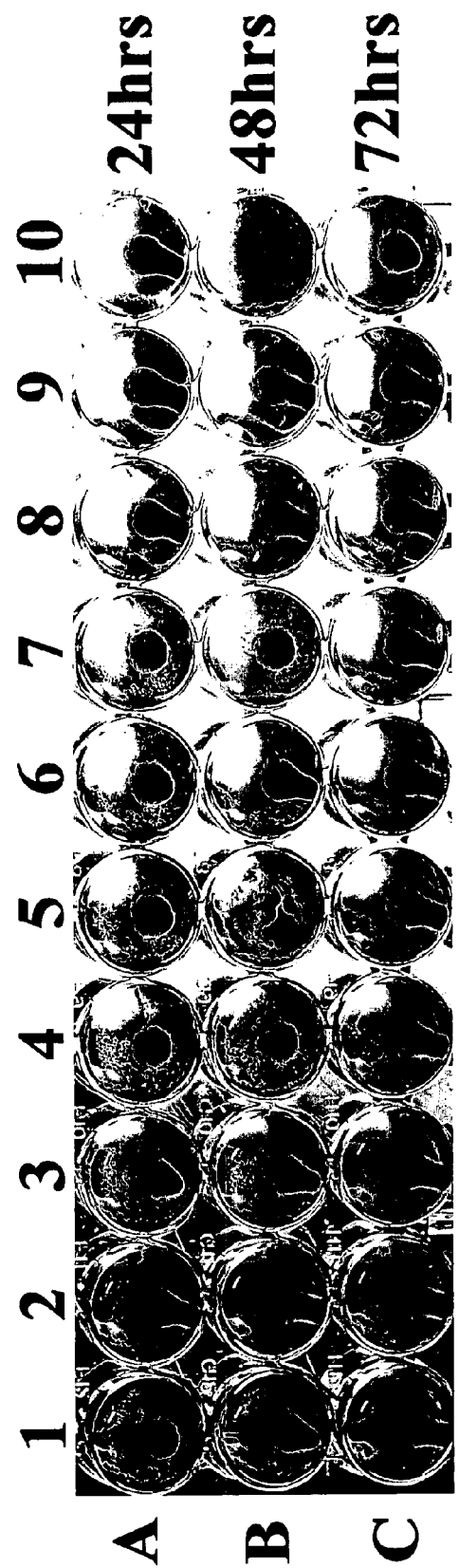
FIG. 8 is a graphical representation of prevention of MDCK cell infection with influenza A virus strain H1N1 by anti-virus antibodies and human sera.
Figure 9:
FIG. 9 is a graphical representation of prevention of cell MDCK infection with influenza A virus strain H3N1 by anti-virus antibodies and human sera
Figure 10:
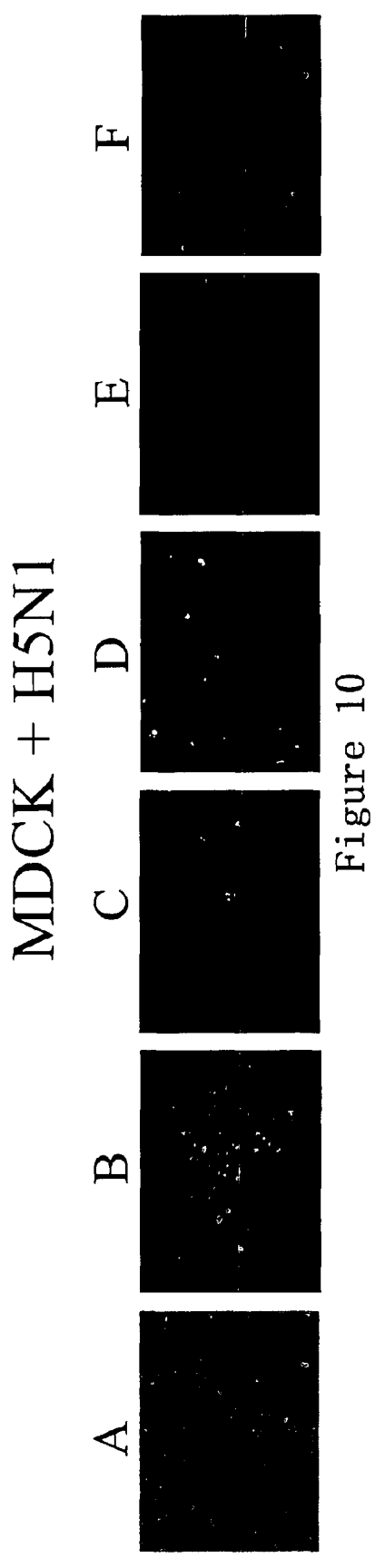

A cell or tissue culture assay can be used to determine the function of a mimic antigen or molecule binding to an antibody against a pathogen. Cell lines sensitive to infectious agents known in the art, and also primary cells or tissues or organs (targets of viral infections, for example) can be cultured with a selected antibody for a period time sufficient for the antibody to bind to the mimic antigens or molecules existing on the cells or tissues or organs, the free antibodies not binding to the mimic antigens or molecules should be washed off, and the cells or tissues or organs are infected with the infectious pathogen (a virus strain, for example). The infection of the pathogen can be detected in a variety of ways well known to those of ordinary skill in the art (for example, determination of the titer of a virus strain). In the case that the mimic molecule is the receptor or factors related to the entry or infection of the pathogen, the antibody can block the mimic antigen or molecule and prevent the entry or infection of the pathogen into the cells or tissues or organs. Thereof the cells or tissues or organs will not be or lightly infected by the pathogen. Example of prevention of influenza virus infection with anti-influenza antibodies in a cell line system is as described as in the part of Exemplification of the application (FIG. 8-10).

Purification and Identification of a Mimic Antigen

In another embodiment, a simple method for purification of a functionally important mimic antigen or molecule comprises of using a selected antibody preferably monoclonal antibody against a pathogen. This approach eliminates laborious screening work for an interested antigen as regularly used in the filed of protein purification. According to the invention, sera, lysates or extract of available related cells, tissues and/or organs of humans, animals or plants as mentioned above, can be used for purification of a mimic antigen in a variety of ways well known to those of ordinary skill in the art.

Identification of the sequence or structure of a mimic antigen, key molecules being related to the binding of a mimic antigen and a given antibody, agonists and antagonists of a mimic antigen in a variety of ways well known to those of ordinary skill in the art is also included in the present invention.

Another subject of the present invention is the use of the identified mimic molecules thereof and/or their derivatives according to the present invention in animal experiments and/or cell or tissue culture systems as illustrated above for the detection of the function of the identified mimic molecules and their derivatives, and for screening candidate derivatives of a mimic antigen for prevention and treatment of a related disorder in vivo.

The mimic antigens or molecules according to the present invention can be a protein; glycoprotein; glycan; polypeptides; polysaccharides; oligosaccharides; lipid, glycolipid; carbohydrate; lectin, selectin; mucin; hemagglutinin, collagen, keratin, receptor including viral receptors, toll-like receptor; cellular component; oncogene product; fragments of mammalian cells therefrom including tumor cells, or any other substances without limitation. A key feature of the molecular mimicry according to the present invention is that mimic antigens or molecules can be receptors, coreceptors or factors related to viral infections, target antigens of autoimmune diseases, or tumor related antigens, and the antibodies against these mimic antigens can be inducers of autoimmune diseases or cancers.

Candidate agents for molecular mimicry are glycans and recognition system of glycans which is closely linked to the origin of life and its evolution. The term glycan refers to a polysaccharide, or oligosaccharide. Glycan may also be used to refer to the carbohydrate portion of a glycoconjugate, such as a glycoprotein, glycolipid, or a proteoglycan. Glycans usually consist solely of O-glycosidic linkages of monosaccharides. Monosaccharides commonly found in eukaryotic glycoproteins include glucose, N-acetylglucosamine, galactose, N-acetylgalactosamine, mannose, fucose, xylose and N-acetylneuraminic acid (also known as sialic acid). Glycans can be found attached to proteins as in glycoproteins and proteoglycans. They are generally found on the exterior surface of cells. O- and N-linked glycans are very common in eukaryotes but may also be found, although less commonly, in prokaryotes.

Recognition system of glycans includes but not limited to lectins, enzyme containing carbohydrate recognition domain (CRD), antibodies against glycans, cytokines, chaperone and transport proteins. Lectins occur ubiquitously in nature. Lectins are known to play important roles in the immune system by recognizing carbohydrates that are found exclusively on pathogens, or that are inaccessible on host cells. Pathogenic lectins from virus, bacteria, and protozoa are involved in infection through their sialic acid-recognizing activity. One of the best studied examples is hemagglutinin of influenza in which the virus utilizes sialic acids on the cell surface of the host during infection.

Sialic acid is a generic term for the N- or O-substituted derivatives of neuraminic acid, a nine-carbon monosaccharide. It is also the name for the most common member of this group, N-acetylneuraminic acid (Neu5Ac or NANA). Sialic acids are found widely distributed in animal tissues and in bacteria, especially in glycoproteins and gangliosides. The amino group bears either an acetyl or a glycolyl group. The hydroxyl substituents may vary considerably: acetyl, lactyl, methyl, sulfate and phosphate groups have been found. Sialic acid rich glycoproteins bind selectin (C-type lectin) in humans and other organisms.

Animal glycan-recognizing proteins can be broadly classified into two groups-lectins (which typically contain an evolutionarily conserved carbohydrate-recognition domain [CRD]) and sulfated glycosaminoglycan (SGAG)-binding proteins. The biosynthesis of structurally complex GAG is regulated and its diverse sulfation pattern is formed organ-and tissue-specifically as well as temporally during growth and development. Proteins other than antibodies and T-cell receptors that mediate glycan recognition via immunoglobulin (Ig)-like domains are called "I-type lectins." The major homologous subfamily of I-type lectins with sialic acid (Sia)-binding properties and characteristic amino-terminal structural features are called the "Siglecs" (Sia-recognizing Ig-superfamily lectins).

Mucins can be sialic acid-containing glycoproteins. Mucins are secreted in the mucus of the respiratory and digestive tracts. Mucin genes encode mucin monomers that are synthesized as rod-shape apomucin cores that are post-translationally modified by exceptionally abundant glycosylation. Two distinctly different regions are found in mature mucins: 1) The amino- and carboxy-terminal regions are very lightly glycosylated, but rich in cysteines, which are likely involved in establishing disulfide linkages within and among mucin monomers. 2) A large central region formed of multiple tandem repeats of 10 to 80 residue sequences in which up to half of the amino acids are serine or threonine. This area becomes saturated with hundreds of O-linked oligosaccharides. N-linked oligosaccharides are also found on mucins, but much less abundantly. At least 19 human mucin genes have been distinguished by cDNA cloning—MUC1, 2, 3A, 3B, 4, 5AC, 5B, 6-9, 11-13, and 15-19. The major secreted airway mucins are MUC5AC and MUC5B, while MUC2 is secreted mostly in the intestine but also in the airway. Increased mucin production occurs in many adenocarcinomas, including cancer of the pancreas, lung, breast, ovary, colon, etc. Mucins are also over expressed in lung diseases such as asthma, bronchitis, COPD or cystic fibrosis.

Utilities of Molecular Mimicry

Molecular mimicry according to the present invention has several utilities. All the utilities are suitable for humans, animals and plants.

Molecular Mimicry and Infections

One utility is a useful tool in understanding the etiology, pathogenesis, treatment, and prevention of infections. The location of an antigenic or molecular mimicry can be major determinants of tropism of an infectious agent, limiting the host range among different species and organ or tissue range in a same species. For example, anti-RSV antibodies bind to an mimic antigen expressed on lung instead of small intestine of newborn pups; anti-rotavirus polyclonal antibodies bind to an mimic antigen expressed on the surface of small intestine rather than lung of newborn pups (FIG. 2), consisting to the organ tropism of RSV and rotavirus infections (small intestine or lung respectively).

The expressive diverse pattern of a mimic antigen or molecules can be formed temporally during growth and development. A mimic antigen or molecule can be expressed large presence in embryo and fetal decreases with growth or through the intact period of life time. This can explain the age-dependent nature of some infections that only affect infants and young children. For example, both antibodies to rotavirus and RSV bind to lung and small intestine of newborn pups rather than those organs of adult mice (FIG. 2 and FIG. 4), consisting to the age nature of rotavirus and RSV infections (target infants or young children only). In contrast, antibodies against influenza A virus bind to lungs and small intestines of both newborn pups and adult (FIG. 2 and FIG. 4), consisting to the fact that influenza infection target all ages of a target biological organism (a mouse or a human for example).

Alternatively, the characteristics pattern of a mimic antigen or molecules can be formed organ-and tissue-specifically. For example, antibodies against rotavirus bind to small intestine rather than lung of newborn pups (organ-specific, FIG. 2); highly fucosalated glycans are found specifically in small intestine whereas the sulfo-Le$^x$ determinant carrying core 2 glycans is recovered mainly in the distal colon (Robbe et al., Biochem. J. (2004) 384, 307-316) (tissue-specific). Such qualitative differences can be related to the nature of rotavirus infection.

Other expressive patterns of molecular mimicry are as described as in the part of Exemplification of the application.

Importantly, understanding of a new organ tropism of an infection is therapeutically useful in the development of vaccines and treatments that can control antiviral responses. For example, strong binding of anti-HIV antibodies to small intestine of mouse pups and adult (FIG. 2 and FIG. 4) discloses a new organ tropism that can be related to a novel viral reservoir of HIV and/or a novel pathogenic mechanisms of HIV infection. Thus, new therapeutic methods or vaccines for prevention, diagnosis, and treatment of HIV can be developed based on the disclosure. Similarly, binding of anti-HAV and -HBV antibodies to small intestine of human fetal is detected (FIG. 1). This simple and rapid method for detection of tissue tropism of molecular mimicry can be extended to identify new organ tropisms of other infectious pathogens.

Molecular Mimicry and Autoimmune Disorders

Another utility is a useful tool in understanding the etiology, pathogenesis, treatment, and prevention of autoimmune disorders. Autoimmune diseases occur when the immune system erroneously senses that normal tissue is foreign and attacks it. Molecular mimicry has been characterized as recently as the 1970's as a mechanism by which a pathogen can generate autoimmunity. Either the linear amino acid sequence or the conformational fit of the immunodominant epitope may be shared between the pathogen and host. This is also known as "cross-reactivity" between self antigen of the host and immunodominant epitopes of the pathogen. An autoimmune response is then generated against the epitope. Due to similar sequence homology in the epitope between the pathogen and the host, cells and tissues of the host associated with the protein are destroyed as a result of the autoimmune response. One of the most prevalent immunological participants in autoimmune destruction is autoantibodies.

The HIV-1 virus has been shown to cause diseases of the central nervous system (CNS) in humans through a molecular mimicry apparatus. Antibodies produced for the HIV-1 gp41 protein can cross-react with astrocytes within human CNS tissue and act as autoantibodies (Yamada et al., J. Virol. (1991), 65: 1370-1376). Myasthenia gravis is another common autoimmune disease. Cross-reactivity of the self epitope (α-subunit of the receptor) with antibodies produced against herpes simplex virus (HSV) suggests that the virus is associated with the initiation of myasthenia gravis (Oleszak et al., Clin. Microbiol. Rev. (2004), 17: 174-207). In the case of most autoimmune diseases in humans however, there is no compelling evidence that the antigenic cross-reactivity identified in laboratory studies are of pathogenic importance (Mackay et al., New. Engl. J. Med. (2001), 345, 340-350). According to the present invention, all the antigenic cross-reactivity identified are pathogenic important because all the antibodies are neutralizing antibodies to each relevant pathogen.

According to the present invention, mimic antigens or molecules can intensively exist on and/or in normal tissue of a biological organism and can be the targets of antibodies induced to pathogenic agents during and/or after infections or vaccinations. This can lead to many types of autoimmune diseases, including but not limited to Kawasaki's disease, biliary atresia, primary biliary cirrhosis, systemic lupus erythematosus, Sjogren's syndrome, rheumatoid arthritis, juvenile onset diabetes mellitus, Hodgkin's and non-Hodgkin's lymphoma, malignant melanoma, cryoglobulinemia, hepatitis B virus infection, hepatitis C virus infection, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, autoimmune hemolytic anemia, dermatitis herpetiformis, alopecia greata, autoimmune cystitis, pemphigoid, scieroderma, progressive systemic sclerosis, CREST syndrome (calcinosis, Raynaud's esophageal dysmotility, sclerodactyl), and telangiectasia), adult onset diabetes mellitus (Type II diabetes), male or female autoimmune infertility, ankylosing spondylitis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, pemphigus vulgaris, pemphigus, bullous pemphigoid, postcardotomy syndrome, Cushing's syndrome, autoimmune chronic active hepatitis, bird-fancier's lung, asthma, allergic disease, allergic encephalomyelitis, toxic necrodermal lysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, chronic fatigue syndrome, fibromyalgia, Takayasu's arteritis, polymyalgia rheumatica, temporal arteritis, schistosomiasis, giant cell arteritis, ascariasis, aspergillosis, Sampter's syndrome (triaditis also called, nasal polyps, eosinophilia, and asthma), Behcet's disease, Caplan's syndrome, dengue, encephalomyositis, endocarditis, myocarditis, endomyocardial fibrosis, endophthalmitis, erythema elevatum et diutinum, psoriasis, erythroblastosis fetalis, fascitis with eosinophilia, Shulman's syndrome, Felty's syndrome, filariasis, cyclitis, chronic cyclitis, heterochromic cyclitis, Fuch's cyclitis, IgA nephropathy, Henoch-Schonlein purpura, glomerulonephritis, graft versus host disease, transplantation rejection, cardiomyopathy, Alzheimer's disease, parvovirus infection, rubella virus infection, post vaccination syndromes, congenital rubella infection, renal cell carcinoma, multiple myeloma, Eaton-Lambert syndrome, relapsing polychondritis, Waldenstrom's macroglobulinemia, mumps virus infection, thrombotic throbocytopenic purpura and any other disorder in which the specific recognition of the host by immunoglobulin, B cell surface receptor (surface immunoglobulin), or T cell receptor is suspected or shown to be important in any aspect of the pathogenesis of the clinical illness.

Therefore, antibodies induced during an infection can be the causes of autoimmune diseases. Antibodies induced during an infection usually reach a pick level at 2-3 weeks of an acute infection when the infectious pathogen is cleared and an autoimmune disease can be raised through attacking a mimic antigen in the host by the antibodies. The tissue or organ tropism of a mimic antigen is useful to screen candidate pathogens causing autoimmune diseases. For example, antibodies against adenovirus, EBV and CMV bind to multiple organs such as lung, kidney, spleen, and small intestine (as shown in FIG. 2-6), they can be related to lupus, diabetes, or kidney and heart disorders such as but not limited to hemolytic uremic syndrome and nephritic syndrome. Another example is that anti-adenovirus antibodies bind to small blood vessels of multiple organs (FIG. 2-6) thus is highly suspect to diseases with inflammation of blood vessels such as but not limited to Kawasaki disease. Therefore, detection of these antibodies against both pathogens and mimic antigens of host is a useful tool to determine the causes of and to diagnose autoimmune diseases.

Molecular Mimicry and Cancers, Obesity, and Other Disorders

Another utility is a useful tool in understanding the etiology, pathogenesis, treatment, and prevention of cancers, obesity, and other disorders. In biology, signal transduction refers to any process by which a cell converts one kind of signal or stimulus into another, most often involving ordered sequences of biochemical reactions inside the cell, that are carried out by enzymes and linked through second messengers resulting in what is thought of as a "second messenger pathway". Many disease processes such as diabetes, heart disease, autoimmunity, cancer and obesity arise from defects in signal transduction pathways. Cell-surface receptors are integral transmembrane proteins and recognize the vast majority of extracellular signaling molecules. Binding of a ligand to a cell-surface receptor stimulates a series of events inside the cell with different types of receptor stimulating different intracellular responses. In eukaryotic cells, most intracellular proteins activated by a ligand/receptor interaction possess an enzymatic activity. Many of the enzymes are activated as part of the signal transduction mechanism. Specific example receptors in the present invention include but not limited to G-protein coupled receptors (e.g. Chemokine receptors), receptor tyrosine kinases (e.g. Growth factor receptors), integrins and toll-like receptors, fibroblast growth factor receptor (FGFR) family, v RET receptor family, vascular endothelial growth factor receptor (VEGFR) family. Receptor tyrosine kinases (RTK) have been shown to be not only key regulators of normal cellular processes but also to have a critical role in the development and progression of many types of cancer (Roskoski et al., (2004), Biochem. Biophys. Res. Commun. 319: 1-11). Diseases such as diabetes and certain forms of pituitary cancer, among many others, are thought to have some root in the malfunction of G proteins (Wikipedia, the free encyclopedia). The pathogenesis of infectious disease and tumor growth, have close ties with Toll-like receptor (TLR) signaling pathways (Wikipedia, the free encyclopedia). These receptors can act as mimic antigens and be triggered by the antibodies raised in an infection. Some antibodies can induce defects in signal transduction pathways that lead to the development and progression of many types of cancer, obesity and other disorders.

Candidate antibodies that induce defects in signal transduction pathways can be screened and identified using cellular or tissue culture systems and animals described above, and cell lines derived from cancer cells or cancer tissues as described as in the part of Exemplification of the application.

The Mechanisms of Vaccination and Passive Immunity and New Vaccines

Another utility is a useful tool in understanding the mechanisms of vaccination and passive immunity and development of new vaccines. A vaccine is an antigenic preparation used to establish immunity to a disease. The immune system recognizes vaccine agents as foreign, destroys them, and 'remembers' them. When the virulent version of an agent comes along, the immune system is thus prepared to respond, by (1) neutralizing the target agent before it can enter cells, and (2) by recognizing and destroying infected cells before that agent can multiply to vast numbers. Both functional mechanisms of a vaccine are to target the vaccine agents or the infectious agent. Passive immunity is the transfer of active humoral immunity in the form of readymade antibodies, from one individual to another. Passive immunization is used when there is a high risk of infection and insufficient time for the body to develop its own immune response, or to reduce the symptoms of ongoing or immunosuppressive diseases. The functional mechanism of a passive immunity or immunoglobulin therapy is currently explained as same as that of a vaccine. However, most molecules, including antibodies, only remain a short period of time in the circulation because they are captured by vascular endothelial cells and then efficiently destroyed by a process referred to as catabolism. Therefore, it is unlikely that a vaccine or a passive immunity function mainly based on free antibodies in circulation.

The existence of a receptor for IgG molecules which greatly slows catabolism of the IgG molecules has been previously proposed. U.S. Pat. No. 6,992,234 directly demonstrated a protective effect of endothelial receptor FcRn on IgG destruction. The receptor is postulated to do this by binding most IgG molecules before they are destroyed, and then recycling the antibodies back into the bloodstream thereby increasing the half-life of IgG. According to the present invention, a mimic antigen or molecule can act as a receptor for antibodies induced in vaccination or from a passive immunity. This binding of an antibody to a mimic antigen not only prevent the pathogen's entry into target cells, but also protect the antibody from being destroyed rapidly and then recycling the antibodies back into the bloodstream thereby increasing the half-life of the antibody. This mechanism can be the major functional mechanism of vaccines and passive immunity.

The usual large number of phenotypes of a given infectious agent makes vaccine preparation difficult, especially for the pathogens with a large variety of strains. There is surprisingly only couple of receptors on the cell surface to which representatives of one or other group of an infectious agent can bind. The presence of only a few receptors offers promising possibilities for the successful combating of an infection. Since receptors are generally highly specific, there is a possibility of achieving controlled influence on the receptors by means of suitable substances, for example by blocking the receptors. If substances which block the receptor are used, the penetration of receptor-specific viruses into the cell can be prevented. The same substances which can prevent infection in this way can also be used for the treatment of a manifest infection. Most of mimic antigens or molecules according to the invention can be such receptors and/or ligands of an infectious pathogen. For example, a glycoprotein can be a receptor for a virus and a sialic acid on the protein as a ligand for the pathogen lectin (recognize the sialic acid on the protein). Therefore, vaccine preparation can be significantly simplified by focusing on couple of receptors or ligands shared by all the strains of a given pathogen regardless the complicated variety of strains or phenotypes of a given pathogen.

For example, a sialic acid vaccine or a hemagglutin vaccine, can protect infections of viruses with hemagglutin as their envelope protein. The antibodies induced by such vaccines can react to both pathogens and receptor on hosts that is different from viral receptor-based protection of viral infections described in U.S. Pat. Nos. 5,712,245 and 5,929,220 (antibodies react to host only). This "receptor vaccine" and/or "ligand vaccine" can be developed at pathogen-basic and avoiding the difficulties of host-based identification and purification of receptor and overcomes the difficulty of vaccine development due to various strains or phenotypes of a pathogen especially for a pathogen with a large variety of strains.

Notably, the present invention discloses for the first tine that different pathogens can share same or similar receptors. As shown in FIG. 8, infection of MDCK cells with influenza virus strains H1N1 is prevented by antibodies not only to strain H1N1 but also strains H3N1 and H5N1, and antibodies to different pathogens of RSV, adenovirus and HAV. FIG. 9 shows that infection of MDCK cells with influenza virus strains H3N1 is prevented by antibodies not only to strain H3N1 but also strains H1N1 and H5N1; FIG. 10 shows that binding of inactivated H5N1 strain to MDCK cells is prevented by antibodies not only to strain H5N1 but also strain H1N1 and antibodies to different pathogens of RSV and rotavirus. Based on this invention, a vaccine to pathogen A can be protective not only against the A infection but also against infections caused by pathogens B, C, D and etc. This "Multiple-pathogen vaccine" further simplifies the process of vaccine preparation and significantly reduces the cost for the prevention of infections.

According to the invention, the candidate immunogens for a receptor-vaccine and/or ligand-vaccine and/or pathogen-universal vaccine includes but not limited to envelope proteins of infectious agents, viral attachment proteins including hemagglutinin, neuraminidase, G protein, M protein, pathogenic lectins from virus, bacteria, and protozoa, glycans; sialic acids, sialic acid-containing glycoconjugates, glycoproteins; polypeptides; polysaccharides; oligosaccharides; glycolipid; carbohydrates; lectins including R-type, M-type, P-type, L-type, C-type and I-type lectins; calnexins; galectins; mucins; hemagglutinins, keratins, carbohydrate recognition domains in enzymes (CRD).

The traditional vaccination is aimed to stimulate high level of antibodies against a vaccine. Because antibodies induced during and/or after vaccination can cause autoimmune diseases even cancers, the aim of vaccination should be corrected to yield efficacy of blocking without much extra free antibodies. A vaccine is preferably provided to a biological organism through its natural infecting routes. For example, an influenza vaccine can be provided by oral and inhalant approaches; rotavirus vaccine is preferably administrated by an oral approach.

Molecular Mimicry-Based Prevention and Treatment

The present invention also extends to a strategy for developing novel methods of prevention, diagnosis, and treatment for the relevant disorders, obtainable based on the antigens being identified. All the methods are suitable for humans, animals and plants.

As used herein, "prevention" is any activity which reduces the burden of mortality or morbidity from disease. This takes place at primary, secondary and tertiary prevention levels. Primary prevention avoids the development of a disease. Secondary prevention activities are aimed at early disease detection, thereby increasing opportunities for interventions to prevent progression of the disease and emergence of symptoms. Tertiary prevention reduces the negative impact of an already established disease by restoring function and reducing disease-related complications.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

Figure 11:
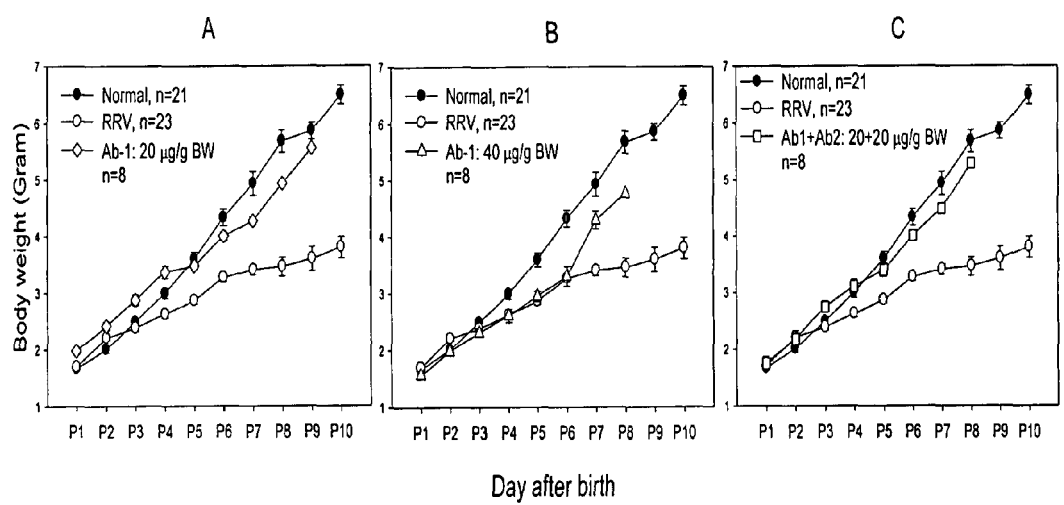
FIG. 11 is a graphical representation of body weight curves of mouse pups treated with antibodies to rotavirus before rotavirus infection.

One subject of the present invention is the use of antibodies against pathogens and mimic antigens or molecules existing in humans, animals or plants for the prevention (antibody prevention) and treatment (antibody therapy) of the related infections. The antibody prevention and antibody therapy according to the present invention is an effective, simple and rapid tool to control a pandemic infection during the outbreak seasons of the relevant infection. According to the present invention, a mimic antigen or molecule can act as a receptor of an infectious agent, an existing antibody to the pathogen or an antibody being produced to the pathogen or the mimic antigen can be administrated to a biological organism, preferably an individual, and/or an animal during the outbreak season of the relevant infection. The antibody will bind to the mimic antigen or molecule in/on the biological organism, block the receptor, and the penetration of the pathogen into the cells expressing the antigen can be prevented. The same substances which can prevent an infection in this way can also be used for the treatment of the same infection when the antibody is administrated to the biological organism during early stage of the infection. One example using antibodies against rotavirus for prevention and treatment of rotavirus infection is shown in FIG. 11-13.

The antibody prevention and therapy in the present invention are not limited to use of one kind of antibody, combination of multiple antibodies to one infectious agent (for example anti-A.1+anti-A.2) or different antibodies to different infectious agents (for example anti-B and/or anti-C) can be used to prevent and treat an infection (A infection). One example using combined two kinds of antibodies against rotavirus for prevention of rotavirus infection is shown in FIG. 11-13. Another example shows that in a cell line (MDCK) culture system, infection of influenza virus H3N1 is prevented by antibodies to multiple influenza virus strains H1N1, H3N1 and H5N1 (FIG. 9). Another example shows that in the same cell line (MDCK) culture system, infection of influenza virus H1N1 is prevented by antibodies not only to influenza virus strains H1N1 and H3N1, but also antibodies to other viruses such as RSV, HAV, and adenovirus (FIG. 8). Another example shows that in the same cell line (MDCK) culture system, binding of inactivated influenza virus H5N1 is prevented by antibodies not only to influenza virus strains H1N1 and H5N1, but also to other viruses such as RSV, and rotavirus (FIG. 10). The antibody prevention and antibody therapy illustrated above is an effective, simple and rapid tool to control a pandemic infection such as but not limited to avian influenza.

The artificial induction of passive immunity has been used for over a century to treat infectious disease such as diphtheria, tetanus, botulism, hepatitis A, hepatitis B, smallpox, measles, rabies, vaccinia. Immunoglobulin therapy has been used for both prevention and treatment of severe respiratory diseases, infections of herpes simplex virus (HSV), varicella zoster virus, Epstein-Barr virus (EBV), and cytomegalovirus (CMV). During the 1918 "Spanish flu" pandemic, transfusion of human blood products from recovering patients was associated with a 50% reduction of the infection mortality. During a 1995 Ebola virus outbreak in Congo, whole blood from recovering patients containing anti-Ebola antibodies, was used to treat eight patients. Only one of the eight patients died, compared to a typical 80% Ebola mortality. In recent years, passive immunity-based antibody therapy has been used in mice for both prevention and treatment of influenza including H5N1 influenza. Two such studies were reported after the filling date of the provisional application of the present invention (Hanson et al., Respiratory Research (2006), 7:126; Simmons et al., PloS. Med. (2007), 4(5): e178). All these treatment are based on the mechanisms of passive immunity that is aimed to neutralize the infectious agent.

According to the present invention, the use of an antibody to an infectious agent or a mimic antigen or molecule for antibody prevention or antibody therapy of an infection is based on a mechanism targeting and blocking a mimic antigen or molecule existing in a host that cab be related to the entry of an infectious agent (the receptor or co-receptor or ligand). This mechanism is distinct from the existing traditional mechanisms of vaccine and passive immunity as illustrated above.

Another subject of the present invention is the use of the antibodies against pathogenically mimic antigens related to autoimmune diseases caused by the pathogenic infections for the prevention of the autoimmune disorders. For example, an autoimmune disease caused by an infection can be prevented by administration of low dose antibodies to the pathogen of the infection to block the mimic antigen. The dosage regimen utilizing antibodies for this purpose is the amount within the range that yields efficacy of blocking without much extra free antibodies. This use of specific and low-dose antibodies for the prevention of the autoimmune disorders according to the present invention is distinct from the use of non-specific and high-dose immunoglobulin for the therapy of autoimmune diseases that is aimed to dilute the concentration of an autoantibody or interrupt the specific binding of the autoantibody.

As used herein, "derivatives" refers to compounds that at least theoretically can be formed from the precursor compound; "analog" or "analogue" refers to a substance which is similar in structure to another substance; "agonist" refers to a substance that binds to a specific receptor and triggers a response in the cell. It mimics the action of an endogenous ligand that binds to the same receptor. A "partial agonist" activates a receptor, but only produces a partial physiological response compared to a full agonist. They may also be considered as a ligand which displays both agonistic and antagonistic effects. A co-agonist works with other co-agonists to produce the desired effect together. An "antagonist" blocks a receptor from activation by agonists. Receptors can be activated or inactivated either by endogenous (such as hormones and neurotransmitters) or exogenous (such as drugs) agonists and antagonists, resulting in stimulating or inhibiting the cell. New findings that broaden the conventional definition of pharmacology demonstrate that ligands can concurrently behave as agonist and antagonists at the same receptor, depending on effector pathways.

Another subject of the present invention is the use of derivatives, analogs, agonists or antagonists, variants, mutants, or fragments of a pathogenically mimic antigen existing in humans, animals or plants for the prevention and treatment of the related disorders such as infections, autoimmune diseases, cancers, obesity and other disorders. For example, to a mimic antigen as a receptor of a viral infection, an analog or agonist of the antigen can be administrated to the biological organism preferably an individual, and/or an animal during the outbreak season of the relevant infection. The agonist or antagonist will bind to the mimic antigen either in/on the biological organism or on the virus, block the penetration of the virus into the cell expressing the antigen. The same substances which can prevent infection in this way can also be used for the treatment of the same infection. Similarly, antagonists of mimic antigens can be used to prevent and treat autoimmune diseases and cancers by blocking a receptor from activation. The dosage regimen for this purpose is the amount within the range that yields efficacy of blocking without much extra. The dosage range is usually low.

Candidates of the derivatives, analogs, agonists or antagonists variants, mutants, or fragments of a mimic antigen or molecule includes but not limited to glycans including mannose, galactose, N-acetylgalactosamine, glucose and N-acetylglucosamine; sialic acids, plant lectins including mannose-, galactose-, N-acetylgalactosamine-, glucose- and N-acetylglucosamine-specific plant agglutinines, glycoproteins; polypeptides; polysaccharides; oligosaccharides; glycolipid; carbohydrates; lectins including R-type, M-type, P-type, L-type, C-type and I-type lectins; calnexins; galectins; mucins; hemagglutinins, carbohydrate recognition domains in enzymes (CRD). The derivatives of a mimic antigen such as tissue extracts, synthetic peptides recombinant antigens or other forms of the antigen can also be used for the treatment of a related disease.

Another subject of the present invention is the use of inactivated particles or fragments or extracts of a pathogenic reagent which shares a mimic antigen with a biological organism for the prevention and treatment of the related infections. For example, inactivated particles or fragments or extracts of a virus which shares a host mimic antigen related to the viral entry into the host can be administrated to the host during the relevant infection. The inactivated particles or fragments or extracts of the virus will bind to the mimic antigen in/on the host, block and/or compete for the receptor, and the penetration of the virus into the cell expressing the antigen can be prevented. The dosage regimen utilizing inactivated particles or fragments or extracts of an infectious agent for this purpose is the amount within the range that yields efficacy of saturation without immunization. This use of inactivated particles or fragments or extracts of an infectious agent for treatment according to the present invention is distinct from the traditional vaccination using dead virus as a vaccine that is aimed to stimulate immune responses.

Another subject of the present invention is the use of inactivated particles or fragments or extracts of a pathogen which cause an autoimmune disease or cancer or obesity or other diseases for treatment of the related disorders. For example, low dose of inactivated particles or fragments or extracts of a pathogen or a mimic antigen related to an autoimmune disease can be administrated to the biological organism suffering from the autoimmune disease. The inactivated particles or fragments or extracts of the pathogen or the mimic antigen will neutralize the autoantibody against the mimic antigen in the biological organism, block and/or reduce the attack of the autoantibody to the cells expressing the mimic antigen. The derivatives of a mimic antigen such as tissue extracts, synthetic peptides, recombinant proteins or other forms of the antigen can also be used for the treatment of a related autoimmune disease. The dosage regimen utilizing inactivated pathogen or extracts of a pathogen or derivatives of a mimic antigen for this purpose is the amount within the range that yields efficacy of neutralizing without immunization. This use of inactivated pathogen or extracts of a pathogen or derivatives of a mimic antigen for treatment according to the present invention is distinct from the traditional vaccination using high-dose inactivated pathogen as an immunogen that is aimed to stimulate immune responses.

Another subject of the present invention is the use of a pathogenically mimic antigen and/or its antibodies which causes an autoimmune disease for diagnosis of the autoimmune disease, cancers and other related disorders. Kits containing pathogens or mimic antigens obtained through the process of the present invention and/or antibodies to the pathogens or mimic antigens can be prepared in a variety of ways well known to those of ordinary skill in the art. Such kits are used to detect the presence of the antibody to the antigen in a biological sample.

According to the present invention, pharmaceutically useful compositions comprising the mimic antigens and/or their antibodies, the homologs or analogs or antagonists, effective derivatives of the antigen, synthetic peptides, recombinant proteins or any other forms of the antigen of the present invention can be formulated, according to known methods such as by the admixture of a pharmaceutically acceptable carrier. Such compositions will contain an effective amount of the antigens or other forms of the antigen and/or their antibodies to form a pharmaceutically acceptable composition suitable for effective administration.

The dosage regimen utilizing the mimic antigens or molecules and/or their antibodies, the analogs or antagonists, effective derivatives of the antigens, synthetic peptides, recombinant antigens or any other forms of the antigens according to the present invention is selected in accordance with a variety of factors including location and density of the antigen, type, species, age, weight, sex and medical condition of the patient; the severity of the condition to be treated; the route of administration; the renal and hepatic function of the patient; and the particular substances thereof employed. Optimal precision in achieving concentrations of the said substances of the present invention within the range that yields efficacy without toxicity requires a regimen based on the kinetics of the thereof employed substance availability to target sites. This involves a consideration of the distribution, equilibrium, and elimination of the thereof employed substances of the present invention.

The present invention also has the objective of providing suitable topical, oral systemic and parenteral pharmaceutical formulations for use in the novel methods of prevention and treatment. The compositions containing the mimic antigens and/or their antibodies, the analogs or antagonists, effective derivatives of the antigen, synthetic peptides, recombinant proteins or any other forms of the antigens identified as the active ingredient can be administered in a wide variety of therapeutic dosage forms in conventional vehicles for administration. For example, the said antigens and/or their antibodies can be administered in such oral dosage forms as tablets, capsules (each including timed release and sustained release formulations), pills, powders, granules, elixirs, tinctures, solutions, suspensions, syrups and emulsions, or by injection. The pharmaceutical compositions can be provided to a biological organism by a variety of routes such as subcutaneous, topical with or without occlusion, oral, intramuscular, intravenously (both bolus and infusion), intraperitoneally, intramuscularly, subcutaneously, intracavity, or transdermally, inhalant, or other using forms well known to those of ordinary skill in the pharmaceutical arts.

The final subject of the present invention is the uses of the molecular mimicry identified to the fields of epidemiology and developmental and evolutionary biology. “Epidemiology” is the study of factors affecting the health and illness of populations, and serves as the foundation and logic of interventions made in the interest of public health and preventive medicine. In evolutionary biology, homology is any similarity between characters that is due to their shared ancestry. Shared ancestry can be evolutionary or developmental. Evolutionary ancestry means that structures evolved from some structure in a common ancestor. Developmental ancestry means that structures arose from the same tissue in embryonal development. Epidemiology is the study of factors affecting the health and illness of populations, and serves as the foundation and logic of interventions made in the interest of public health and preventive medicine. It is considered a cornerstone methodology of public health research, and is highly regarded in evidence-based medicine for identifying risk factors for disease and determining optimal treatment approaches to clinical practice. The molecular mimicry between microorganisms and other different species is a useful tool for the studies of epidemiology and developmental and evolutionary biology.

The foregoing specification describes only the preferred embodiments and/or alternate embodiments of the disclosure. Other embodiments besides the above may be articulated as well. The terms and expressions therefore serve only to describe the disclosure by example only and not to limit the disclosure. It is expected that others will perceive differences, which while differing from the foregoing, do not depart from the spirit and scope of the disclosure herein described and claimed.

EXEMPLIFICATION

1. Molecular Mimicry Between Viruses and Human and Mice

FIG. 1-7 show examples of molecular mimicry between various viral pathogens and mouse and human tissues or organs, detected by binding of anti-viral antibodies to tissue sections of human fatal, newborn pups and adult mouse and a cell line.

Figure 2:
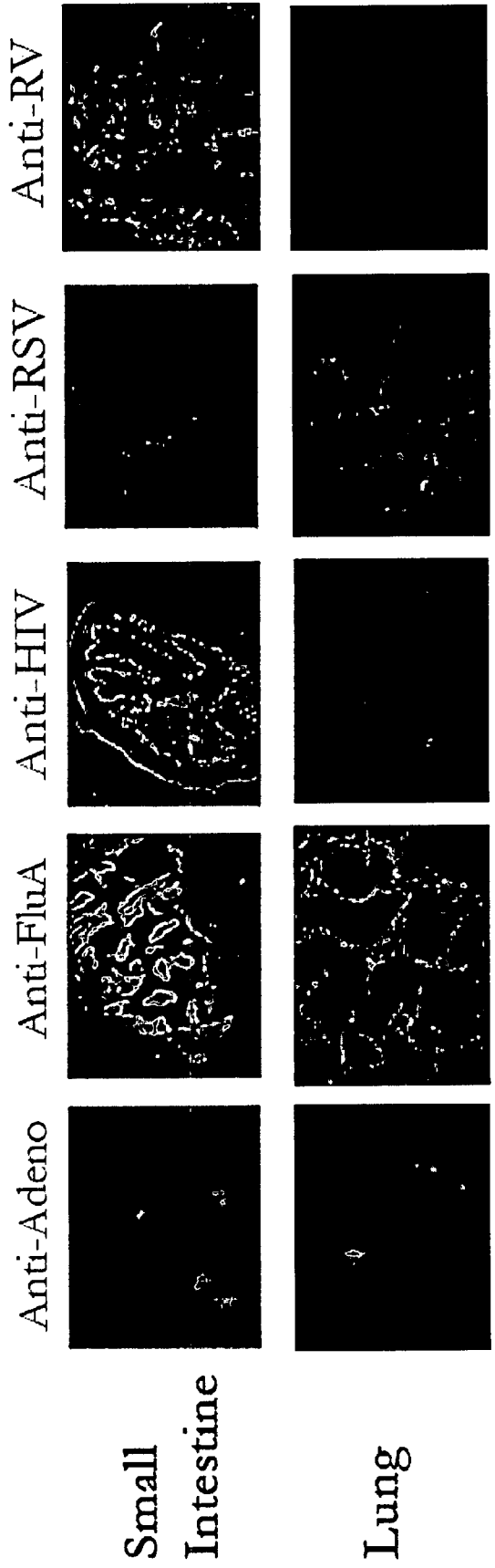
FIG. 2 is a graphical representation of binding of anti-viral antibodies or sera to tissue section of small intestine and lung of bulb/c newborn pups.
Figure 3:
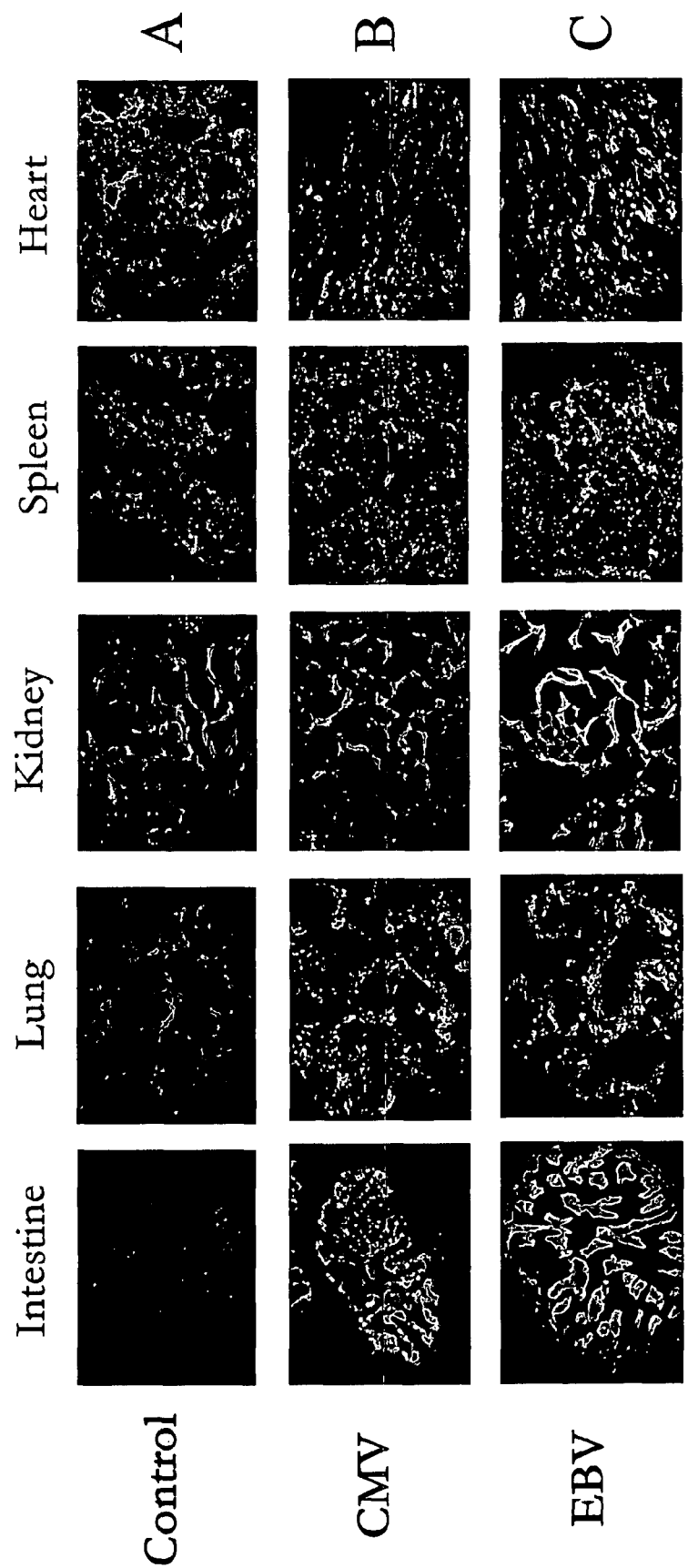
FIG. 3 is a graphical representation of binding of anti-viral antibodies to tissue section of small intestine, lung, kidney, spleen and heart of bulb/c new born pups.
Figure 4:
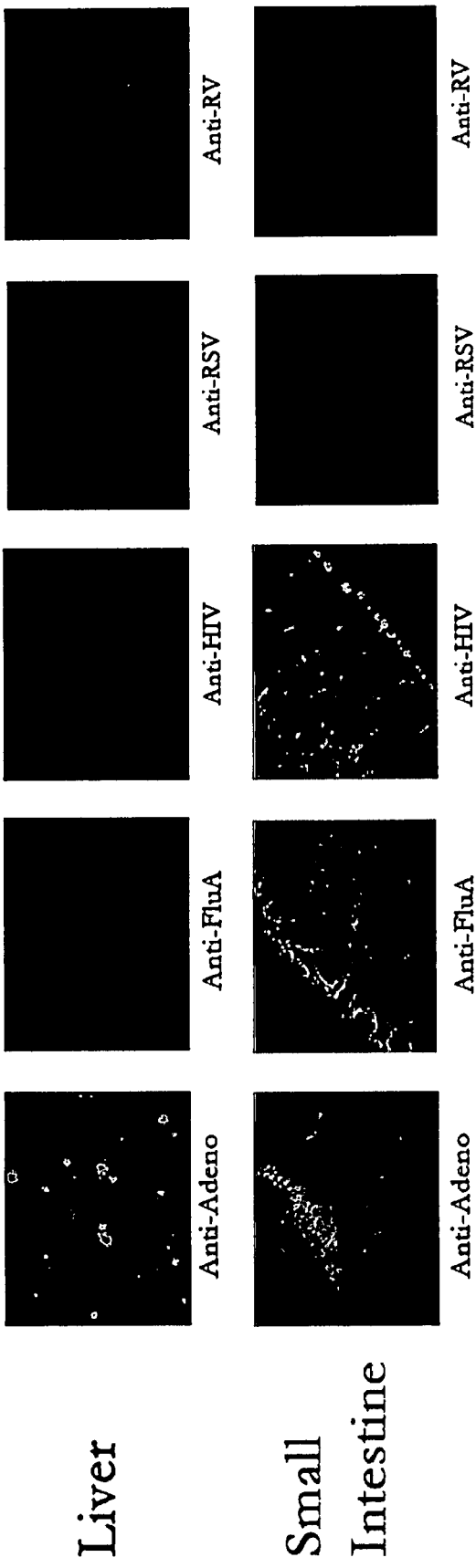
FIG. 4 is a graphical representation of binding of anti-viral antibodies or sera to tissue section of liver and small intestine of bulb/c adult mouse.
Figure 5:
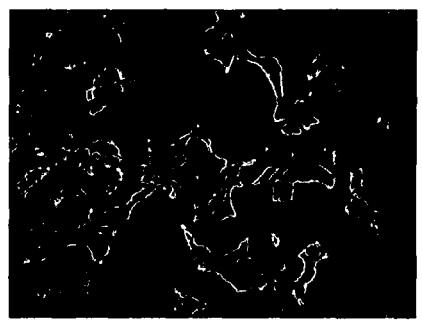
FIG. 5 is a graphical representation of binding of anti-viral antibodies or sera to tissue section of kidney and spleen of bulb/c adult mouse.
Figure 5:
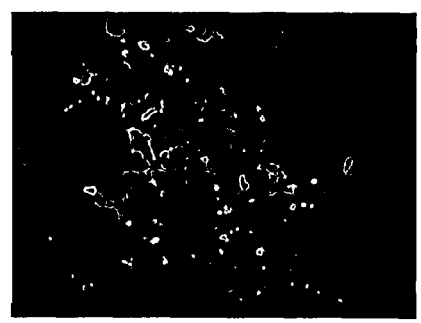
Figure 5:
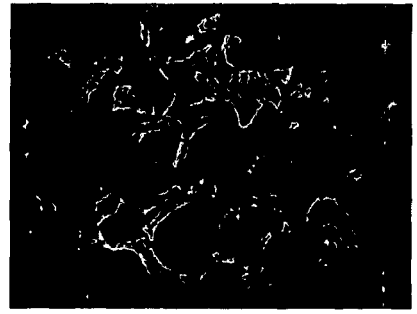
Figure 5:
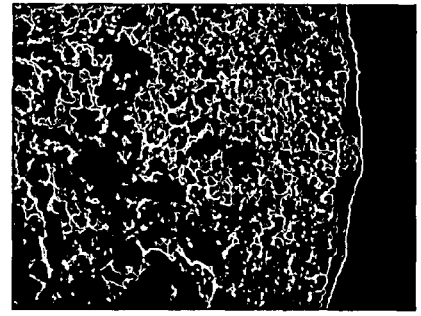
Figure 6:
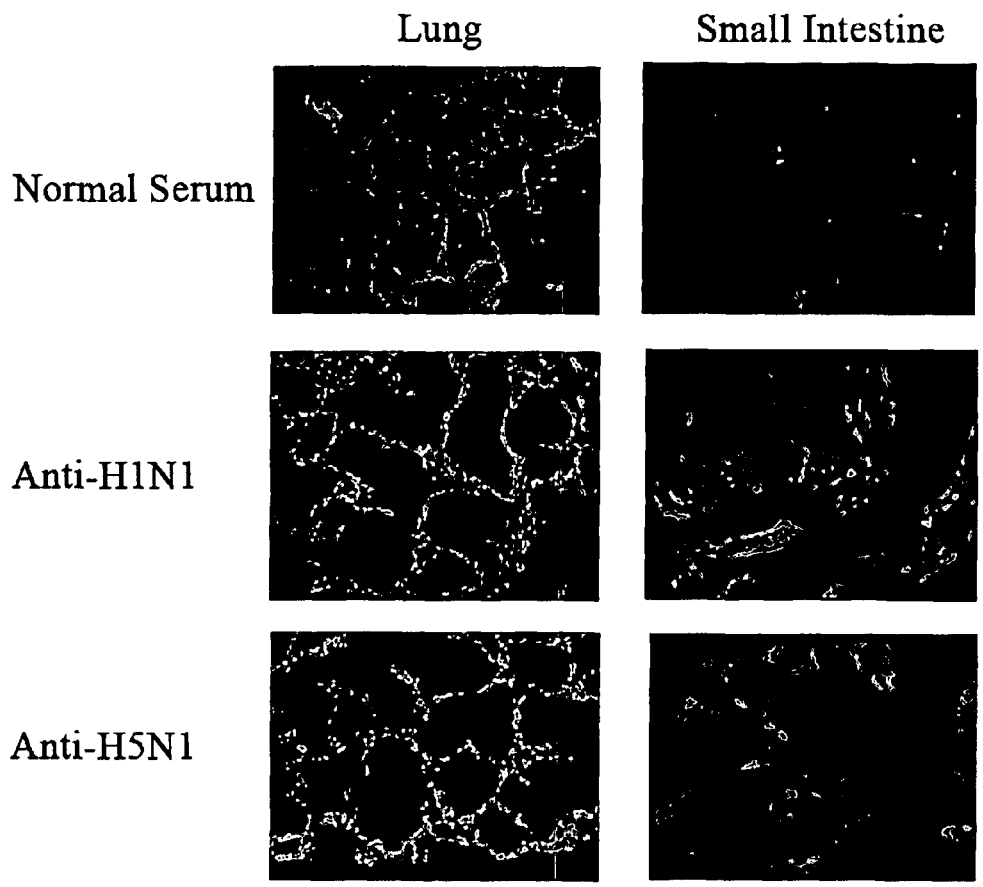
FIG. 6 is a graphical representation of binding of human sera to tissue section of lung and small intestine of bulb/c new born pups.
Figure 7:
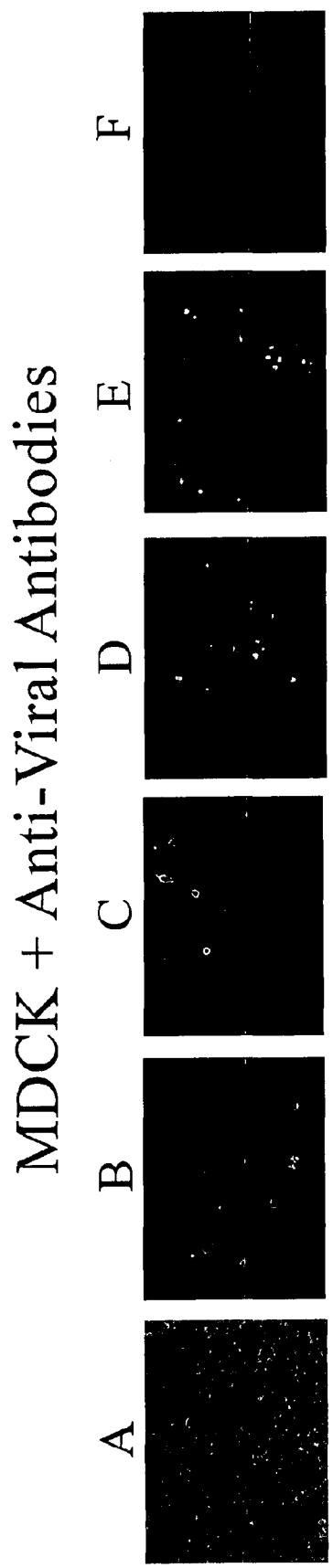
FIG. 7 is a graphical representation of binding of anti-virus antibodies and human serum to a cell line of Madin-Darby canine kidney (MDCK).

Antibodies used include: mouse polyclonal antibodies against adenovirus (Adeno), cytomegalovirus (CMV) rotavirus (QV), and respiratory syncytial virus (RSV); mouse polyclonal antibodies against Epstein-Barr virus (EBV); chicken anti-influenza A virus strain H1N1 (FluA), human anti-human immunodeficiency virus (HIV), -influenza A virus strain H1N1, H3N1 and H5N1, -hepatitis A virus (HAV), and -hepatitis B virus (HBV). All mouse antibodies except anti-EBV polyclonal antibodies were labeled with biotin, and the anti-EBV monoclonal antibodies were labeled with a fluorescent (FITC). The secondary or third reagent for biotin-labeled antibodies was a fluorescent (PE) conjugated-streptavidin that was also used as control of secondary reagent alone without primary antibodies in FIG. 3. Biotin-labeled anti-human IgG antibodies were used as secondary reagent for human sera from H1N1, H3N1 and H5N1 infections Antibodies were incubated with tissue sections of a 26 week human fetal small intestine (FIG. 1), small intestine, lung, kidney, spleen and heart of bulb/c newborn pups (FIG. 2, FIG. 3 and FIG. 6), small intestine and liver of a bulb/c adult mouse (FIG. 4 and FIG. 5), and cells of a Madin-Darby canine kidney (MDCK) cell line (FIG. 7). After wash, streptavidin-PE or biotin-labeled anti-human IgG plus streptavidin-PE was added and incubated for 30 minutes followed by wash and detection with a fluorescent microscope. Positive binding is shown as areas stained brightly and negative binding as areas not stained brightly (dark areas). The patterns of antibody binding to tissue sections or MDCK cell line are described as follows.

a. Single organ-specific and age-dependent pattern: anti-RSV antibodies only bind to lung and anti-RV only to small intestine of a newborn pup (FIG. 2) or human fetal (FIG. 1) rather than those organs of adult mouse.

b. Multiple organ-specific and age-independent pattern: anti-influenza A virus antibodies bind to lung and small intestine but not other tested organs of both newborn pup and adult mouse (FIG. 2 and FIG. 4).

c. Tissue-specific and age-independent pattern: anti-adenovirus antibodies bind to small blood vessels of all tested organs of both newborn pup and adult mouse (FIG. 2, FIG. 4 FIG. 5 and FIG. 6).

d. Systemic and age-independent cross reactivity: antibodies to CMV bind to small intestine, lung, kidney and blood cells of bulb/c newborn pups (FIG. 3 and FIG. 5). Antibodies to EBV bind to small intestine, lung, kidney, and blood cells of both bulb/c newborn pups and adult mice (FIG. 3 and FIG. 5 and FIG. 6).

e. Species limited pattern: Anti-human HAV and -human HBV antibodies bind to small intestine of a human fetal but not to liver of adult mouse (data not shown).

f. Other pattern: antibodies to HIV bind to small intestine of both bulb/c newborn pups and adult mice (FIG. 2 and FIG. 4).

g. Cell line binding: antibodies to Adenovirus, CMV, EBV, influenza H1N1, H3N1, H5N1, HAV, RSV, and RV bind to MDCK cells (FIG. 7 and not shown data). Antibodies to influenza H1N1, RSV, and RV also bind to cells of African Green monkey kidney cell line MA104 (data not shown). FIG. 7A shows the monolayer MDCK cells in the same culture system.

This process will be easily extended to use other antibodies against other viruses and other pathogens and tissue sections of humans, animals, and plants or various cell lines as illustrated above to detect other molecular mimicry existing in humans, animals and plants.

2. Prevention and Treatment of Influenza Infection

Viral Hemagglutination Assay

Many viruses attach to molecules present on the surface of red blood cells. A consequence of this is that—at certain concentrations—a viral suspension may bind together (agglutinate) the red blood cells thus preventing them from settling out of suspension. Usefully, agglutination is rarely linked to infectivity, attenuated viruses can therefore be used in assays.

By serially diluting a virus suspension into an assay tray (a series of wells of uniform volume) and adding a standard amount of blood cells an estimation of the number of virus particles can be made. This assay may be modified to include the addition of an antiserum. By using a standard amount of virus, a standard amount of blood cells and serially diluting the antiserum, one can identify the minimum inhibitory concentration of the antiserum (the greatest dilution which inhibits hemagglutination).

FIG. 8-10 show examples of prevention of influenza A viral infection of MDCK cells. Monolayer of MDCK cells were incubated with various antibodies (1 µg/ml) or sera (1:100 dilution) containing antibodies for one hour, discard the supernatant and wash one time, then challenged with influenza A virus strain H1N1 and H3N1 for one hour, discard the supernatant and change culture medium. The culture supernatant was collected at 24, 48 and 72 hours and used for hemagglutination inhibition test with microtiterplate, chicken red blood cells (RBC) and influenza A virus strains H1N1 (FIG. 8) and H3N1 (FIG. 9).

There are two ways to observe the test results of a viral hemagglutination inhibition test. When look from top of the plate, positive result (inhibiting effect) of the test was observed as RBC pellet at the bottom of a well (FIG. 9 A2-12 and B2-12); negative result (no inhibition) was observed as no RBC or partial pellet at the bottom of a well (FIG. 9 A1 and B1). If turn the plate 90 degree and look from bottom, positive result (inhibiting effect) of the test was observed as tear shape of RBC pellet at the bottom of a well (FIG. 8 A2-3, A8-10, B1-3, B6, B8-10 and C1-9); negative result (no inhibition) was observed as no RBC or no flowing down RBC at the bottom of a well (FIG. 8 A1, A4-7, B4-5, B7, B10, and C10). The result of FIG. 8 and FIG. 9 are summarized in Table 1 and Table 2 separately.

TABLE 1

Infection of MDCK cells with influenza A virus strain H1N1.

| Ab to | Column | | | | | | | | | | |
|---|---|---|---|---|---|---|---|---|---|---|---|
| | 1 H3N1[a] | 2 H1N1[b] | 3 RSV | 4 EBV | 5 RV | 6 Adeno | 7 CMV | 8 HAV | 9 H1N1[c] | 10 — | hrs |
| Inhibition | 1+ | 4+ | 2+ | 1+ | 1+ | 1+ | 1+ | 4+ | 4+ | — | 24 |
| | 3+ | 4+ | 3+ | 1+ | — | 4+ | 1+ | 4+ | 4+ | — | 48 |
| | 4+ | 4+ | 4+ | 4+ | 4+ | 4+ | 4+ | 4+ | 4+ | 2+ | 72 |

Note:
Ab = antibody; immune sera from recovered patients infected with influenza H3N1[a] and H1N1[b], chicken immunized with H1N1[c]; Column 10 was treated with medium alone without antibodies (viral control). The inhibitory effect at 72 hours after infection was due to decreased viral viability.

TABLE 2

Infection of MDCK cells with influenza A virus strain H3N1.

| Ab to | Column | | | | | | | | | | | | |
|---|---|---|---|---|---|---|---|---|---|---|---|---|---|
| | 1 — | 2 H1N1 | 3 H1N1 | 4 H1N1 | 5 H1N1 | 6 H3N1 | 7 H3N1 | 8 H3N1 | 9 H3N1 | 10 H3N1 | 11 H5N1 | 12 H1N1[a] | hrs |
| Inhibition | — | 4+ | 4+ | 4+ | 4+ | 4+ | 4+ | 4+ | 4+ | 4+ | 4+ | 4+ | 48 |
| | — | 4+ | 4+ | 4+ | 4+ | 4+ | 4+ | 4+ | 4+ | 4+ | 4+ | 4+ | 72 |

Note:
immune sera are from different patients recovered from influenza infection of H1N1 H3N1, or chicken immunized with H1N1[a]. Column 1 was treated with medium alone without antibodies (viral control).

The above results show that in a MDCK cellular culture system, infection of influenza virus H3N1 is prevented by antibodies to multiple influenza viral strains H1N1, H3N1 and H5N1 (FIG. 9); that infection of influenza virus H1N1 is prevented by antibodies not only to influenza virus strains H1N1 and H3N1, but also antibodies to other viruses such as RSV, HAV, and adenovirus (FIG. 8).

FIG. 10 shows in the same MDCK cellular culture system, binding of inactivated influenza virus H5N1 is prevented by antibodies not only to influenza virus strains H1N1 (FIG. 10C) and H5N1 (FIG. 10D), but also antibodies to other viruses such as RSV (FIG. 10E) and rotavirus (FIG. 10F) as compared to cells without antibody treatment (FIG. 10B). FIG. 10A shows the monolayer MDCK cells in the same culture system.

A Chicken Embryo Culture System a. A Chicken Embryo Culture System

A chicken embryo culture system will be developed to detect the inhibitory effect of antibodies against influenza infection of various strains including strain H5N1 and antibodies to other pathogens. Middle term chicken embryo will be treated with candidate antibodies at a low dosage within the range that yields efficacy of blocking without much extras, in the ordinary skill in the art; virus inoculation will be performed next day. Candidate antibodies will be also administrated one day after virus inoculation. Rest of experiments including harvesting fluid containing viruses, determining viral titers can be performed in the ordinary skill in the art. Lower viral tiers from chicken embryo culture being treated with antibody compared to controls without antibody treating will indicate a positive effect of prevention or treatment. This system is useful to screen candidate antibodies and other reagents for prevention and treatment of influenza infection in vivo with limited applicable small animal models due to various reasons such as infection with influenza H5N1 strain.

b. A Chicken Embryo Culture System for Detection of Molecular Mimicry

Later term chicken embryo will be treated with candidate antibodies at a high dosage. A candidate antibody can be either purifies or labeled with a moiety. The antibody will bind to its mimic antigen in vivo, followed by scarification of the chicken embryo, collection of tissue or organ samples and detection of the bound antibody in vitro using detection means known in the art. This system is useful to detect molecular mimicry for the infections with limited applicable small animal models due to various reasons such as infection with influenza H5N1 strain.

Animal Experiments

Animals such as mice will be treated with candidate antibodies at a low dosage within the range that yields efficacy of blocking without much extras, in the ordinary skill in the art; virus inoculation will be performed next day. Candidate antibodies will be also administrated one day after virus inoculation. Rest of experiments including evaluate symptoms of infection, determining viral titers can be performed in the ordinary skill in the art. Animals being treated with antibody will be compared to control animals without antibody treating for symptoms of infection, histological changes of organs, and detection of viruses. The process will be useful to evaluate the function of a molecular mimicry and to screen candidate antibodies and other reagents for prevention and treatment of influenza infection in vivo.

3. Prevention and Treatment of Rotavirus Infection

FIG. 11-13 show the prevention and treatment of rotavirus infection by blocking a mimic antigen in small intestine using anti-rotavirus antibodies. Briefly, polyclonal antibodies to rotavirus (Ab-1) alone or combination of Ab-1 and antibodies to inner antigen of rotavirus (Ab-2) were orally administered to sucking pups at day 1 or 2 after birth and challenged with rhesus rotavirus (RRV) 24 hours later (next day). Alternatively, Ab-1 was orally administrated to sucking pups at 24 hours after RRV infection to evaluate the therapeutic effect of antibodies on RRV infection. Pups treated with anti-rotavirus antibodies pre-RRV infection were not or lightly infected and pups treated with antibodies one day after RRV infection recovered sooner compared to the control pups treated with saline and RRV infection, as shown in FIG. 11 (the curve of body weight), FIG. 12 (histological changes of small intestine) and FIG. 13 (immunoflourescent staining for RRV antigen VP6).

FIG. 11 shows growth curve of pups during infection. Antibodies or saline were orally administrated to pups at day 1 (P1) after birth and virus was inoculated orally 24 hours later (P2). Growth of pups treated with 20 µg/g body weight (BW) of Ab-1 (FIG. 11A, open diamond) and pups treated with 20 µg/g BW of each Ab-1 and Ab-2 (FIG. 11C, open square) were not affected compared to control pups treated with saline (FIG. 11, closed circle) and viruses alone (FIG. 11, open circle). Growth of pups treated with 40 µg/g BW of Ab-1 (FIG. 11B, open triangle) was slowed but resumed sooner than control pups treated with viruses alone.

FIG. 12 shows histological changes of small intestine of pups during infection. Day 1 is one day after viral infection. Tissue damage of small intestine of pups treated with antibodies before (FIG. 11, Ab-1+RRV and Ab-1&2+RRV) and after (FIG. 11, RRV+Ab-1) viral infection was less severe than that of pups treated with saline and viruses ((FIG. 11, RRV alone), along with the pups treated with antibodies Ab-1 plus Ab-2 the least damaged.

Consisted to FIGS. 11 and 12, viral antigens were not detectable at day 5 after infection in small intestines of pups treated with antibodies (FIG. 13, Day 5-C, D and E) compared to that of pups without antibody treatment (FIG. 13, Day 5-B). At day 4 after infection, viral antigens were not detectable in small intestines of pups treated with Ab-1 plus Ab-2 (FIG. 13, Day 4-D), lightly detected in small intestines of pups treated with Ab-1 before (FIG. 13, Day 4-C) and after (FIG. 13, Day 4-E) infection, compared to that of pups without antibody treatment (FIG. 13, Day 5-B).

The above observations indicated that combination of two anti-rotavirus antibodies at low dose of each is the most effective way to prevent rotavirus infection and its therapeutic effect will be evaluated with the same mouse model.

4. Treatment of Infections, Autoimmune Diseases and Cancers with Sialic Acid, Sulfates and Plant Lectins a. Cellular Culture Systems for Screening Various amounts of sialic acids, sulfates and plant lectins will be either co-cultured with a viral strain or added certain period time after viral infection (for example 24 hours later), using various cell lines known in the art. Viral titer and viability in the culture medium will be determined with various ways known in the art. Each of sialic acids, sulfates and plant lectins will be administrated in a cellular culture system alone or combined with other reagent together as described as follows.

1) Each sialic acid, sulfate or plant lectin alone
2) sialic acid+sulfate
3) plant lectin+sulfate b. Animal Experiment for Function Detection In Vivo A candidate reagent or combination of reagents will be provided to an animal at thew same time or after a viral infection by a variety of routes such as subcutaneous, topical with or without occlusion, oral, intramuscular, intravenously, intraperitoneally, intramuscularly, subcutaneously, intracavity, or transdermally, inhalant, or other using forms well known to those of ordinary skill in the pharmaceutical arts. Rest of experiments including evaluate symptoms of infection, histological changes, determining viral titers, etc. can be performed in the ordinary skill in the art. Animals being treated with a candidate reagent or a combination of reagents will be compared to control animals without treating for symptoms of infection, histological changes of organs, and detection of viruses. The process will be useful to evaluate the effect of a candidate reagent for treatment of an infection in vivo.

5. Diagnosis of Autoimmune Diseases

Sera from patients diagnosed Kawasaki disease, lupus, diabetes, or kidney and heart disorders such as but not limited to hemolytic uremic syndrome and nephritic syndrome will be screened for antibodies against adenovirus, CMV, EBV and etc. using in the ordinary skill in the art. Antibodies being detected positive will be the candidates for the diseases.

For an organ limited autoimmune disease, for example diabetes, various antibodies to various pathogens will be used to bind to the sections or extract of the organ tissue, for example pancreas. Antibodies being detected bound on pancreas will be the candidate cause for the disease.

6. Identification of Functional Mechanisms of Vaccine and Passive Immunity

Sera from an animal or human immunized with a vaccine or infected with a pathogen at different time points (for example, week 2, 4, 8, 12, 16, etc.) will be detected for the antibodies against the vaccine and the pathogen. Tissue sections from various organs of the animal at matched time points will be used for detection of binding the animal IgG to the tissues or organs by a labeled secondary reagent against the animal IgG. Low level of the antibody in blood and binding of the antibody to a tissue or organ will indicate that binding of antibodies to mimic antigens is the major functional mechanism of a vaccine.

Alternatively, sera from one immunized or infected species (horse for example) will be administrated to another species (mouse for example), and the antibody levels of blood and binding of the antibodies to tissues or organs at various time points will be detected as described above. Low level of the antibody in blood and binding of the antibody to a tissue or organ will indicate that binding of antibodies to mimic antigens is the major functional mechanism of a passive immunity.

7. Development of Receptor or Ligand and Multiple-Pathogen Vaccines a. Cellular Culture Systems for Screening Monolayer of a cell line will be incubated with various antibodies or sera containing antibodies, for one hour, discard the supernatant and wash one time, then being challenged with another pathogen (a virus for example), discard the supernatant and change culture medium. The viral titers will be determined. A pathogen with its antibodies showing inhibitory effect on the viral infection will be a candidate for a multiple-pathogen vaccine. The candidates will be further tested in an animal experiment.

b. Animal Experiment

An animal will be immunized with a vaccine or a pathogen (pathogen A) or be provided with a serum containing antibodies to the pathogen, and infected with at least one other pathogen (pathogen B). Prevention of the infection of the other pathogen will indicate that the vaccine against pathogen A can also protects from pathogen B infection.

Similarly, an animal will be immunized with a candidate immunogen for a receptor or ligand vaccine as described above and infected with various pathogens. Prevention of the infection of the pathogens will indicate that the candidate substance can protect from the infections of those pathogens.

In many cases, a receptor or ligand vaccine can be a multiple-pathogen vaccine.

8. Screening and Identifying Antibodies Inducing Cancers or Obesity

Candidate antibodies will be cultured with cellular or tissue culture systems described above, and cell lines derived from cancer cells or cancer tissues. Candidate antibodies will be also administered to an animal with an experimental cancer. Effect of an antibody on cell proliferation, signal transduction and pathogenesis of a cancer will be compared to a control without antibody treating in a variety of ways well known to those of ordinary skill in the art.

What is claimed is:

1. A method for determining whether antibody that binds to a first virus selected from the group consisting of respiratory syncytial virus, hepatitis A virus, adenovirus, rotavirus, H1N1 influenza virus, H5N1 influenza virus, wherein the first and the second virus are not the same, and H3N1 influenza virus inhibits infection by a second virus selected from the group consisting of H1N1 influenza virus, H3N1 influenza virus, and H5N1 influenza virus, the method comprising:
   administering an antibody to a cell or tissue culture system, wherein the antibody binds to the first virus;
   substantially removing free antibody from said cell or tissue culture system; and
   exposing said cell or tissue culture system to the second virus, wherein an absence or reduced severity of infection with the second virus indicates the presence of an antibody recognizing the first virus capable of inhibiting infection by the second virus.

2. The method of claim 1, wherein the said antibody comprises at least one of an immunoglobulin molecule or an immunologically active portion of an immunoglobulin molecule.

3. The method of claim 1, wherein the second virus and said first virus are as follows, respectively:
   (a) H1N1 influenza virus and respiratory syncytial virus;
   (b) H5N1 influenza virus and respiratory syncytial virus;
   (c) H1N1 influenza virus and hepatitis A virus;
   (d) H1N1 influenza virus and adenovirus;
   (e) H5N1 influenza virus and the rotavirus
   (f) H1N1 influenza virus and a H5N1 influenza virus;
   (g) H1N1 influenza virus and a H3N1 influenza virus;
   (h) H5N1 influenza virus and H1N1 influenza virus;
   (i) H3N1 influenza virus and H1N1 influenza virus;
   (j) H3N1 influenza virus and H5N1 influenza virus.

* * * * *

UNITED STATES PATENT AND TRADEMARK OFFICE
CERTIFICATE OF CORRECTION

PATENT NO. : 8,535,665 B2
APPLICATION NO. : 12/310174
DATED : September 17, 2013
INVENTOR(S) : Huiru Wang It is certified that error appears in the above-identified patent and that said Letters Patent is hereby corrected as shown below:

In the Claims:

In claim 1, at column 25, lines 26-27, please delete “wherein the first and the second virus are not the same,” and insert at column 26, line 2 (after “H5N1 virus,”) -- wherein the first and the second virus are not the same, --.

Signed and Sealed this
Eleventh Day of February, 2014

*Michelle K. Lee*

Michelle K. Lee
*Deputy Director of the United States Patent and Trademark Office*